(12) United States Patent
Stansbury et al.

(10) Patent No.: US 8,727,775 B2
(45) Date of Patent: May 20, 2014

(54) DIMER ACID-DERIVED DIMETHACRYLATES AND USE IN DENTAL RESTORATIVE COMPOSITIONS

(75) Inventors: Jeffrey W. Stansbury, Aurora, CO (US); Christopher N. Bowman, Boulder, CO (US); Marianela Trujillo, Parker, CO (US)

(73) Assignee: The Regents of the University of Colorado, a Body Corporate, Boulder, CO (US)

( * ) Notice: Subject to any disclaimer, the term of this patent is extended or adjusted under 35 U.S.C. 154(b) by 1140 days.

(21) Appl. No.: 11/568,383

(22) PCT Filed: Dec. 29, 2004

(86) PCT No.: PCT/US2004/043828
§ 371 (c)(1),
(2), (4) Date: Aug. 14, 2008

(87) PCT Pub. No.: WO2005/107626
PCT Pub. Date: Nov. 17, 2005

(65) Prior Publication Data
US 2008/0318188 A1 Dec. 25, 2008

Related U.S. Application Data

(60) Provisional application No. 60/566,299, filed on Apr. 28, 2004.

(51) Int. Cl.
*A61C 5/00* (2006.01)
*A61K 6/083* (2006.01)
*C07C 49/84* (2006.01)
*G03F 7/029* (2006.01)
*C08F 299/02* (2006.01)

(52) U.S. Cl.
USPC ............. 433/215; 522/30; 522/44; 522/48; 522/65; 523/116; 526/329.7

(58) Field of Classification Search
USPC ............. 522/30, 44, 48, 65, 215; 523/116; 526/329.7; 433/215
See application file for complete search history.

(56) References Cited

U.S. PATENT DOCUMENTS

| | | | |
|---|---|---|---|
| 3,751,399 A | 8/1973 | Lee et al. | |
| 3,926,906 A | 12/1975 | Lee et al. | |
| 4,544,625 A * | 10/1985 | Ishimaru et al. | 430/284.1 |
| 5,276,068 A | 1/1994 | Waknine | |
| 5,306,739 A * | 4/1994 | Lucey | 522/42 |
| 5,730,601 A | 3/1998 | Bowman et al. | |
| 6,121,358 A * | 9/2000 | Dershem et al. | 524/439 |
| 6,395,803 B1 * | 5/2002 | Angeletakis | 523/116 |

FOREIGN PATENT DOCUMENTS

| | | |
|---|---|---|
| EP | 0 209 700 A2 | 1/1987 |
| EP | 0 209 700 A3 | 1/1987 |
| JP | 02 306955 A | 12/1990 |
| JP | 05 032734 A | 2/1993 |

OTHER PUBLICATIONS

Ge et al., "Design of Low Shrinkage Methacrylate Polymers," Mar. 2003, vol. 44, No. 1, pp. 29-30.*
International Search Report and Written Opinion of the International Searching Authority dated May 17, 2005.
International Preliminary Report on Patentability dated Nov. 9, 2006 prepared by the International Bureau.
Yilmaz et al. (2001) Macromolecular Chemistry and Physics 202(4):532-540 "Preparation and characterization of novel UV-curable urethane methacrylate difunctional monomers and their structure-property relationships".
Supplemental European Search Report mailed Jun. 4, 2010 re: EP04815826.

* cited by examiner

*Primary Examiner* — Michael Pepitone
*Assistant Examiner* — Jessica Roswell
(74) *Attorney, Agent, or Firm* — Merchant & Gould PC

(57) ABSTRACT

The present invention provides polymerizable dental compositions comprising a dimer acid-derived monomer such as a dimer acid-derived di(meth)acrylate monomer. In one embodiment, the dimer acid-derived monomer is of the formula (I): wherein $R_1, R_2, R_3, R_4, R_5$ and $R_6$ are independently selected from H and optionally substituted $C_1$-$C_{25}$ straight-chained or branched aliphatic, optionally containing 1 or more double or triple bonds, wherein one or more carbons are optionally replaced by R* wherein R* is —C(O)—, —C(O)C(O)—, —C(O)NR$^7$—, —C(O)NR$^7$NR$^8$—, —C(O)O—, —OC(O)—, —NR$^7$CO$_2$—, —O—, —NR$^7$C(O)NR$^8$—, —OC(O)NR$^7$—, —NR$^7$NR$^8$—, —NR$^7$C(O)—, —NR$^7$C(O)O—, —S—, —SO—, —SO$_2$—, —NR$^7$—, —SO$_2$NR$^7$— or —NR$^7$SO$_2$—, where R$^7$ and R$^8$ are independently selected from H and optionally substituted aliphatic, cycloalkyl, heterocycloalkyl, aryl or heteroaryl; provided that at least two of $R_1, R_2, R_3, R_4, R_5$ and $R_6$ are substituted $C_{1-25}$ straight-chained or branched aliphatic wherein at least one carbon is replaced by R* and at least one of the substituents is an alkenyl group.

(I)

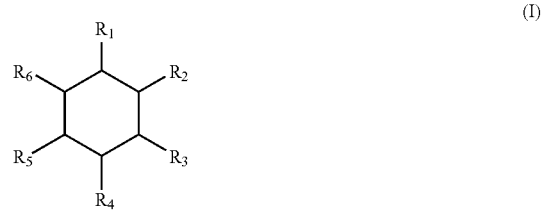

18 Claims, 2 Drawing Sheets

DIMER ACID-DERIVED DIMETHACRYLATES AND USE IN DENTAL RESTORATIVE COMPOSITIONS

CROSS-REFERENCE TO RELATED APPLICATION

This application is a National Stage entry of International Application No. PCT/US2004/043828, filed Dec. 29, 2004, which claims the benefit of U.S. provisional application No. 60/566,299, filed Apr. 28, 2004, the contents of each of which are incorporated herein by reference in their entirety.

STATEMENT REGARDING FEDERALLY SPONSORED RESEARCH OR DEVELOPMENT

This invention was made with government support under grant number DE014227 awarded by The National Institutes of Health. The government has certain rights in the invention.

FIELD OF THE INVENTION

The present invention relates to monomers and more particularly to a dimer acid-derived dimethacrylate polymer system for use as dental restorative resins.

BACKGROUND

Currently, commercial photoactivated dental restorative resins are based on dimethacrylates and the reaction mechanism is through chain-growth free radical polymerization. Existing dimethacrylate systems are popular for fillings and other dental prostheses because of their aesthetic merit and "cure-on-command" feature. Acrylic monomers currently in use generally comprise linear aliphatic or partially aromatic core groups with terminal methacrylate functionality such as 2,2-bis[p-(2'-hydroxy-3'-methacryloxypropoxy)phenyl]-propane (commonly referred to as BisGMA), urethane dimethacrylate UDMA (UDMA; product of 2,2,4(2,4,4)-trimethyl-hexylisocyanate and hydroxyethyl methacrylate) or polyurethane dimethacrylate (PUDMA). As Bis-GMA, PUDMA and other resins are highly viscous at room temperature, they are generally diluted with an acrylate or methacrylate monomer having a lower viscosity, such as trimethylol propyl trimethacrylate, 1,6-hexanediol dimethacrylate, 1,3-butanediol dimethacrylate, and the like. Other diluents include dimethacrylate monomers, such as ethylene glycol dimethacrylate, diethylene glycol dimethacrylate, triethylene glycol dimethacrylate, polyethylene glycol dimethacrylate (PEGDMA) and tetraethylene glycol dimethacrylate. A photoinitiator may be included to provide photoactivity. Dental restorative compositions also typically include silanized filler compounds such as barium, strontium, zirconia silicate and/or amorphous silica to match the color and opacity to a particular use or tooth.

The photoactivated restorative materials are often sold in separate syringes or single-dose capsules of different shades. If provided in a syringe, the user dispenses (by pressing a plunger or turning a screw adapted plunger on the syringe) the necessary amount of restorative material from the syringe onto a suitable mixing surface. The material is then placed directly into the cavity, mold or location of use. If provided as a single-dose capsule, the capsule is placed into a dispensing device that can dispense the material directly into the cavity, mold, etc. After the restorative material is placed, it is photopolymerized, or cured, by exposing the dental restorative composition to the appropriate light source. The resulting cured polymer may then be finished or polished as necessary with appropriate tools. Such dental restoratives can be used for direct anterior and posterior restorations, core build-ups, splinting and indirect restorations including inlays, onlays and veneers.

However, conventional acrylic monomers and indeed their polymers have several critical deficiencies that limit their clinical performance in dental restorative compositions. Existing dimethacrylate monomers and materials demonstrate relatively low conversion, excessive polymerization shrinkage, poor toughness and excessive water uptake. The current systems can only reach a final double bond conversion of 55 to 75 percent, which not only contributes to insufficient wear resistance and mechanical properties, but also jeopardizes the biocompatibility of the composites due to the leachable unreacted monomers. Dimethacrylate based resins exhibit significant volumetric shrinkage during polymerization and the induced shrinkage stress results in tooth-composite adhesive failure, initiating microleakage and recurrent caries, which significantly reduces the longevity and utility of the dental restorative composite. Furthermore, as one tries to increase the final double bond conversion to reduce the unreacted monomers, volumetric shrinkage and shrinkage stress unfortunately also increases, which has been a persisting problem since the development of this class of resins.

Generally, there is a need for dental restorative compositions that are sufficiently viscous to allow easy use but that upon polymerization exhibit lower shrinkage but higher conversion than existing dimethacrylate systems.

SUMMARY OF THE INVENTION

The present invention provides a dimer acid-derived dimethacrylate system with increased conversion, lower shrinkage and reduced odor. Such systems are useful, for example, in dental prosthetic. Accordingly, the present invention provides a polymerizable dental composition comprising a dimer acid-derived monomer. In one embodiment, the dimer acid-derived monomer is a dimer acid-derived di(meth)acrylate monomer. In one embodiment of the invention, the dimer acid-derived monomer is a compound of the formula (I):

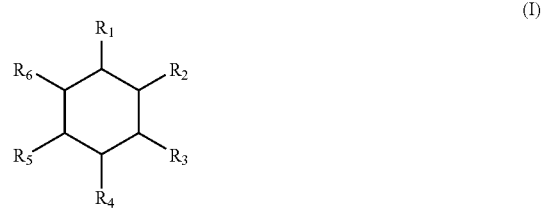

wherein $R_1$, $R_2$, $R_3$, $R_4$, $R_5$ and $R_6$ are independently selected from H and optionally substituted $C_1$-$C_{25}$ straight-chained or branched aliphatic, optionally containing 1 or more double or triple bonds, wherein one or more carbons are optionally replaced by R* wherein R* is —C(O)—, —C(O)C(O)—, —C(O)NR$^7$—, —C(O)NR$^7$NR$^8$—, —C(O)O—, —OC(O)—, —NR$^7$CO$_2$—, —O—, —NR$^7$C(O)NR$^8$—, —OC(O)NR$^7$—, —NR$^7$NR$^8$—, —NR$^7$C(O)—, —NR$^7$C(O)O—, —S—, —SO—, —SO$_2$—, —NR$^7$—, —SO$_2$NR$^7$— or —NR$^7$SO$_2$—, where $R^7$ and $R^8$ are independently selected from H and optionally substituted aliphatic, cycloalkyl, heterocycloalkyl, aryl or heteroaryl. Preferably, at least two of $R_1$, $R_2$, $R_3$, $R_4$, $R_5$ and $R_6$ are substituted $C_{1-25}$ straight-chained or branched aliphatic wherein at least one carbon is replaced by R* and at least one of the substituents is a reactive group, such as an alkenyl group.

According to one embodiment, two of $R_1$, $R_2$, $R_3$, $R_4$, $R_5$ and $R_6$ are H; and two of $R_1$, $R_2$, $R_3$, $R_4$, $R_5$ and $R_6$ are independently optionally substituted $C_1$-$C_{10}$ alkyl. In one embodiment, $R_1$ and $R_2$ are H; and $R_5$ and $R_6$ are independently optionally substituted $C_1$-$C_{10}$ alkyl.

In another embodiment, the alkenyl group is $C_1$-$C_4$ alkenyl, such as (=CH), and is preferably terminally located.

In a further embodiment, $R_3$ and $R_4$ are independently —$(CR^9R^{10})_m$—$C$(=CH)$CH_3$ where at least one of the $CR^9R^{10}$ groups is replaced by R*; m is an integer from 10 to 20; and $R^9$ and $R^{10}$ are independently H, halo, —OH or $C_1$-$C_4$ alkyl. In yet another, $R_3$ and $R_4$ are independently —$(CR^9R^{10})_8$—R*—$(CR^9R^{10})_n$—R*—$C$(=CH)$CH_3$ where n is an integer from 1 to 4, and R* is in each instance independently —C(O)O—, —OC(O)—, —OC(O)NH— or —NHC(O)O—.

Preferably, the dimer acid-derived dimethacrylate monomer is selected from the group consisting of BHEDDMA, DADMA, DANHDMA, DAHEMA, BOHDDMA, HEMA/DDI, mono-BisGMA/DDI and oligomeric BisGMA/DDI.

The composition preferably comprises an initiator, preferably in an amount of from about 0.01 to about 5 weight percent based on the total weight of the composition. The initiator may be any suitable initiator such as, for example, camphorquinone, DMPA or ethyl 4-N,N-dimethaminobenzoate.

In another embodiment of the present invention, the composition further comprises one or more comonomers, where the comonomer comprises at least one functional group. In a further embodiment, the composition comprises two or more comonomers, each comonomer comprising at least one functional group. Exemplary comonomers include bulky monomer, BisGMA, EBPADMA, UDMA, TEGDMA, BHEDDMA, DADMA, DANHDMA, DAHEMA, BOHDDMA, HEMA/DDI, mono-BisGMA/DDI, M'BuDMA-Bisphenol A, D'BuDMA-CH$_2$, BDDMA, PhDMA-Bisphenol A, D'B-DMA-Bisphenol A and oligomeric BisGMA/DDI. According to one aspect of the invention, the dimer acid-derived monomer and the comonomer(s) produce phase-separated, heterogeneous polymeric structures upon polymerization.

The present invention also provide methods of preparing a shaped dental prosthetic device for use in a human mouth comprising: (i) dispensing a mixture including at least one dimer-acid-derived monomer; (ii) shaping the monomer mixture; and (iii) photopolymerizing the monomer mixture to create the shaped dental prosthetic device. In one aspect, the mixture includes at least one comonomer having at least one functional group. In another, the mixture includes at least two comonomers each having at least one functional group.

The present invention also provides a photopolymerizable composition comprising: (i) a dimer acid-derived monomer; and (ii) an initiator. The composition may further comprise one or more additional monomers each having at least one functional group, where the dimer acid-derived dimethacrylate monomer and the one or more additional monomers produce a phase separated polymer structure with the optical properties dependent on the phase separated morphology and domain dimensions.

DETAILED DESCRIPTION

Figure 1:
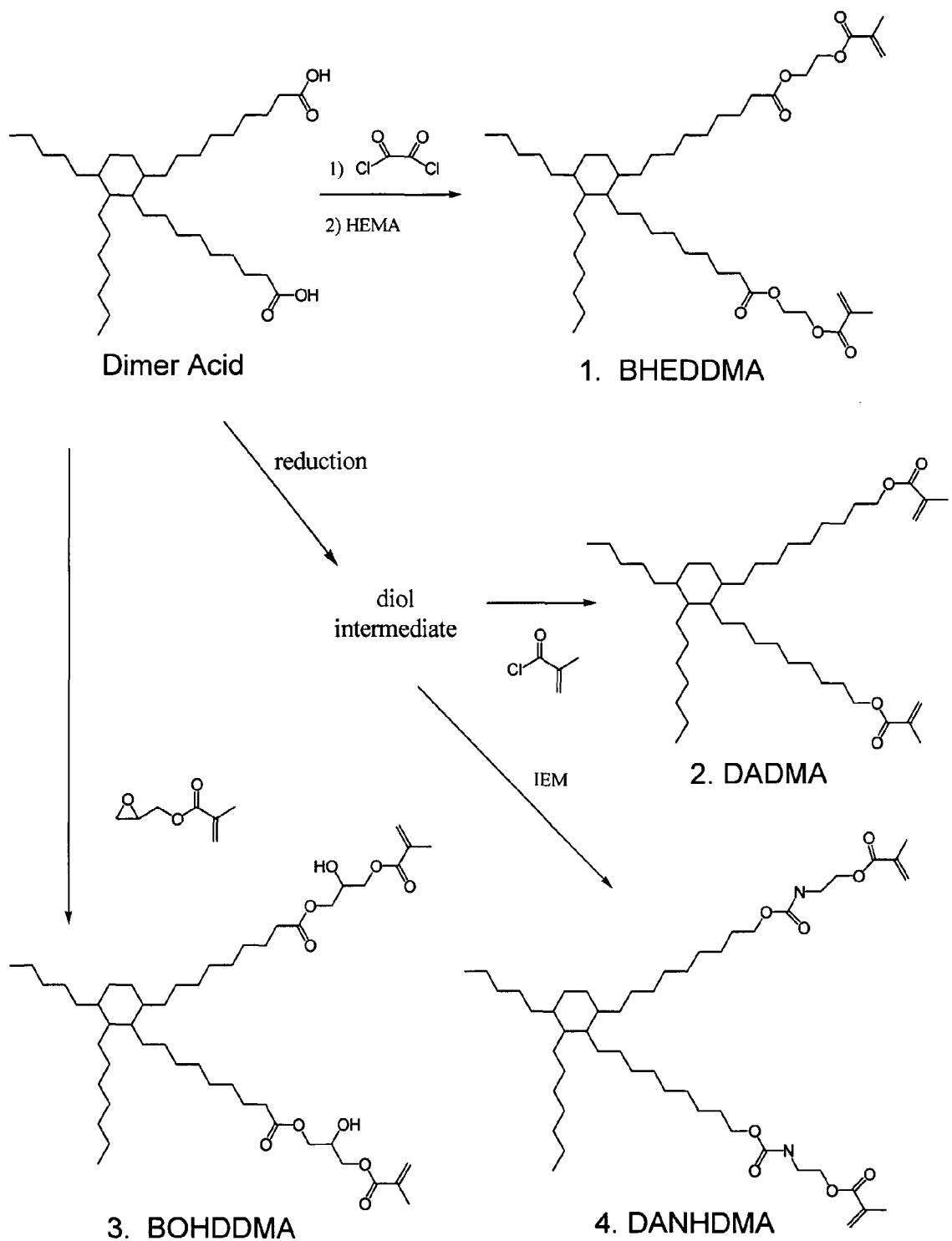
FIG. 1 is a diagram showing a dimer acid starting material and exemplary dimer acid-derived dimethacrylate monomers obtained from various reaction routes.

As used herein, the following definitions shall apply unless otherwise indicated.

The phrase "optionally substituted" is used interchangeably with the phrase "substituted or unsubstituted." Unless otherwise indicated, an optionally substituted group may have a substituent at each substitutable position of the group, and each substitution is independent of any other. Also, combinations of substituents or variables are permissible only if such combinations result in stable compounds. In addition, unless otherwise indicated, functional group radicals are independently selected. Where "optionally substituted" modifies a series of groups separated by commas (e.g., "optionally substituted A, B or C"; or "A, B or C optionally substituted with"), it is intended that each of the groups (e.g., A, B and C) is optionally substituted.

The term "aliphatic" or "aliphatic group" as used herein means a straight-chain or branched $C_{1-12}$ hydrocarbon chain that is completely saturated or that contains one or more units of unsaturation, or a monocyclic $C_{3-8}$ hydrocarbon or bicyclic $C_{8-12}$ hydrocarbon that is completely saturated or that (contains one or more units of unsaturation, but which is not aromatic (also referred to herein as "carbocycle" or "cycloalkyl"), that has a single point of attachment to the rest of the molecule wherein any individual ring in said bicyclic ring system has 3-7 members. For example, suitable aliphatic groups include, but are not limited to, linear or branched or alkyl, alkenyl, alkynyl groups and hybrids thereof such as (cycloalkyl)alkyl, (cycloalkenyl)alkyl or (cycloalkyl)alkenyl.

The terms "alkyl," "alkoxy," "hydroxyalkyl," "alkoxyalkyl" and "alkoxycarbonyl," used alone or as part of a larger moiety include both straight and branched chains containing one to twelve carbon atoms. The terms "alkenyl" and "alkynyl" used alone or as part of a larger moiety shall include both straight and branched chains containing two to twelve carbon atoms.

The terms "haloalkyl," "haloalkenyl" and "haloalkoxy" means alkyl, alkenyl or alkoxy, as the case may be, substituted with one or more halogen atoms. The term "halogen" or "halo" means F, Cl, Br or I.

The term "heteroatom" means nitrogen, oxygen, or sulfur and includes any oxidized form of nitrogen and sulfur, and the quaternized form of any basic nitrogen.

The term "aryl" used alone or in combination with other terms, refers to monocyclic, bicyclic or tricyclic carbocyclic ring systems having a total of five to fourteen ring members, wherein at least one ring in the system is aromatic and wherein each ring in the system contains 3 to 8 ring members. The term "aryl" may be used interchangeably with the term "aryl ring". The term "aralkyl" refers to an alkyl group substituted by an aryl. The term "aralkoxy" refers to an alkoxy group substituted by an aryl.

The term "heterocycloalkyl," "heterocycle," "heterocyclyl" or "heterocyclic" as used herein means monocyclic, bicyclic or tricyclic ring systems having five to fourteen ring members in which one or more ring members is a heteroatom, wherein each ring in the system contains 3 to 7 ring members and is non-aromatic.

The term "heteroaryl," used alone or in combination with other terms, refers to monocyclic, bicyclic and tricyclic ring systems having a total of five to fourteen ring members, and wherein: 1) at least one ring in the system is aromatic; 2) at least one ring in the system contains one or more heteroatoms; and 3) each ring in the system contains 3 to 7 ring members. The term "heteroaryl" may be used interchangeably with the term "heteroaryl ring" or the term "heteroaromatic". Examples of heteroaryl rings include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 1-pyrazolyl, 3-pyrazolyl, 4-pyrazolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indazolyl, isoindolyl, acridinyl, and benzoisoxazolyl. The term "heteroaralkyl" refers to an alkyl group substituted by a heteroaryl. The term "heteroarylalkoxy" refers to an alkoxy group substituted by a heteroaryl.

An aryl (including aralkyl, aralkoxy, aryloxyalkyl and the like) or heteroaryl (including heteroaralkyl, heteroarylalkoxy and the like) group may contain one or more substituents. Suitable substituents on an unsaturated carbon atom of an aryl, heteroaryl, aralkyl or heteroaralkylgroup are selected from halogen; haloalkyl; —$CF_3$; —R; —OR; —SR; 1,2-methylenedioxy; 1,2-ethylenedioxy; protected OH (such as acyloxy); phenyl (Ph); Ph substituted with R; —O(Ph); —O-(Ph) substituted with R; —$CH_2$(Ph); —$CH_2$(Ph) substituted with R; —$CH_2CH_2$(Ph); —$CH_2CH_2$(Ph) substituted with R; —$NO_2$; —CN; —$N(R)_2$; —NRC(O)R; —NRC(O)$N(R)_2$; —$NRCO_2R$; —NRNRC(O)R; —NR—NRC(O)$N(R)_2$; —$NRNRCO_2R$; —C(O)C(O)R; —C(O)$CH_2$C(O)R; —$CO_2R$; —C(O)R; —C(O)$N(R)_2$; —OC(O)$N(R)_2$; —$S(O)_2$R; —$SO_2N(R)_2$; —S(O)R; —$NRSO_2N(R)_2$; —$NRSO_2R$; —C(=S)$N(R)_2$; —C(=NH)—$N(R)_2$; —$(CH_2)_y$NHC(O)R; —$(CH_2)_y$R; —$(CH_2)_y$NHC(O)NHR; —$(CH_2)_y$NHC(O)OR; —$(CH_2)_y$NHS(O)R; —$(CH_2)_y$NHSO_2R$; or —$(CH_2)_y$NHC(O)CH((V)$_z$—R)(R) wherein each R is independently selected from hydrogen, optionally substituted $C_{1-6}$ aliphatic, an unsubstituted 5-6 membered heteroaryl or heterocyclic ring, phenyl (Ph), —O(Ph), or —$CH_2$(Ph)-$CH_2$(Ph), wherein y is 0-6; z is 0-1; and V is a linker group. When R is $C_{1-6}$ aliphatic, it may be substituted with one or more substituents selected from —$NH_2$, —NH($C_{1-4}$ aliphatic), —N($C_{1-4}$ aliphatic)$_2$, —S(O)($C_{1-4}$ aliphatic), —$SO_2$($C_{1-4}$ aliphatic), halogen, ($C_{1-4}$ aliphatic), —OH, —O—($C_{1-4}$ aliphatic), —$NO_2$, —CN, —$CO_2H$, —$CO_2$($C_{1-4}$ aliphatic), —O(halo $C_{1-4}$ aliphatic), or -halo($C_{1-4}$ aliphatic); wherein each $C_{1-4}$ aliphatic is unsubstituted.

An aliphatic group or a non-aromatic heterocyclic ring may contain one or more substituents. Suitable substituents on a saturated carbon of an aliphatic group or of a non-aromatic heterocyclic ring are selected from those listed above for the unsaturated carbon of an aryl or heteroaryl group and the following: =O, =S, =NNHR, =$NN(R)_2$, =N—, =NNHC(O)R, =NNHCO$_2$(alkyl), =$NNHSO_2$(alkyl), or =NR, where each R is independently selected from hydrogen or an optionally substituted $C_{1-6}$ aliphatic. When R is $C_{1-6}$ aliphatic, it may be substituted with one or more substituents selected from —$NH_2$, —NH($C_{1-4}$ aliphatic), —N($C_{1-4}$ aliphatic)$_2$, halogen, —OH, —O—($C_{1-4}$ aliphatic), —$NO_2$, —CN, —$CO_2H$, —$CO_2$($C_{1-4}$ aliphatic), —O(halo $C_{1-4}$ aliphatic), or -halo($C_{1-4}$ aliphatic); wherein each $C_{1-4}$ aliphatic is unsubstituted.

Substituents on a nitrogen of a non-aromatic heterocyclic ring are selected from —R, —$N(R)_2$, —C(O)R, —C(O)OR, —C(O)C(O)R, —C(O)$CH_2$C(O)R, —$SO_2R$, —$SO_2N(R)_2$, —C(=S)$N(R)_2$, —C(=NH)—$N(R)_2$ or —$NRSO_2R$; wherein each R is independently selected from hydrogen, an optionally substituted $C_{1-6}$ aliphatic, optionally substituted phenyl (Ph), optionally substituted —O(Ph), optionally substituted —$CH_2$(Ph), optionally substituted —$CH_2CH_2$(Ph), or an unsubstituted 5-6 membered heteroaryl or heterocyclic ring. When R is a $C_{1-6}$ aliphatic group or a phenyl ring, it may be substituted with one or more substituents selected from —$NH_2$, —NH($C_{1-4}$ aliphatic), —N($C_{1-4}$ aliphatic)$_2$, halogen, —($C_{1-4}$ aliphatic), —OH, —O—($C_{1-4}$ aliphatic), —$NO_2$, —CN, —$CO_2H$, —$CO_2$($C_{1-4}$ aliphatic), —O(halo $C_{1-4}$ aliphatic) or -halo($C_{1-4}$ aliphatic); wherein each $C_{1-4}$ aliphatic is unsubstituted.

As used herein, "dimer acid" means any of the class of cycloaliphatic carboxylic acids that are high-molecular-weight dibasic acids which are liquid (viscous), and which can be polymerized directly with alcohols and polyols to form polyesters. Dimer acids may be produced by dimerization of unsaturated fatty acids at mid molecule and often contains 36 carbon atoms. In addition to the dicarboxylic acid functionality, dimer acids can be dervivatized to include diisocyanate, diol or diepoxide derivatives of dimer acids. The dimer acid may be a $C_{36}$ to $C_{44}$ aliphatic diacid such as those prepared by the oxidative coupling of $C_{18}$ to $C_{22}$. unsaturated monoacids. For simplicity, only the $C_{36}$ dimer acid will be discussed in detail in this specification, as one skilled in the art will be able to modify the teachings herein equally to other dimer acids.

As used herein, a "dimer acid-derived monomer" or "dimer acid-based monomer" means any monomer created using a dimer acid as a starting material and reacting, in one or more steps, the dimer acid with one or more materials to form a derivative monomer capable of free radical polymerization. FIG. 1 shows several examples of dimer acid-derived monomers created by different reaction paths. The term also includes compounds of formula (I) where $R_1$, $R_2$, $R_3$, $R_4$, $R_5$ and $R_6$ are defined above. Preferably, at least two "R" groups are substituted $C_1$-$C_{25}$ straight-chained or branched aliphatic comprising as one of the substituents a reactive group, such as an alkenyl group. Preferably, the alkenyl group will be terminally located on the "R" group. Preferably, the substituted $C_1$-$C_{25}$ straight-chained or branched aliphatic will have at least one carbon replaced by R*, as defined above.

Figure 2:
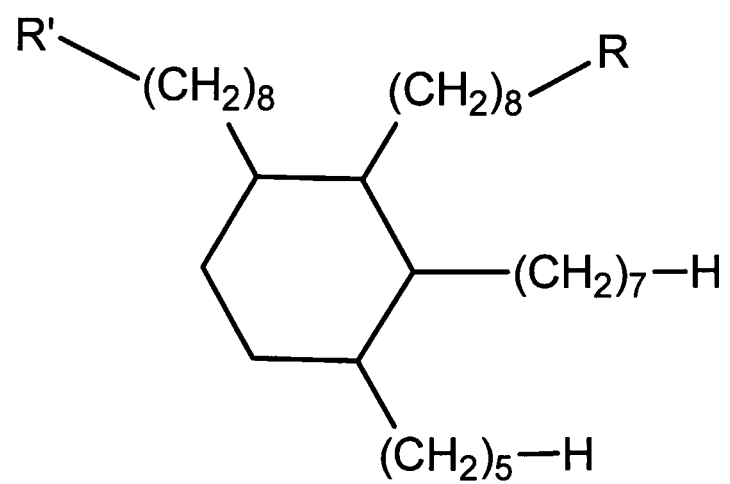
FIG. 2 is a diagram of a general structure of a dimer acid-derived monomer.

According to one embodiment of formula (I), at least two of $R_1$, $R_2$, $R_3$, $R_4$, $R_5$ and $R_6$ are substituted $C_{1-25}$ straight-chained or branched aliphatic wherein at least one carbon is replaced by R* and at least one of the substituents is an alkenyl group; at least two of $R_1$, $R_2$, $R_3$, $R_4$, $R_5$ and $R_6$ are H; and at least two of $R_1$, $R_2$, $R_3$, $R_4$, $R_5$ and $R_6$ are unsubstituted alkyl groups. One such embodiment is represented by the structure shown in FIG. 2 where one or both of R and R' comprise at least one functional group, i.e., a polymerizable double bond. According to one embodiment, R and R' are the same moiety.

Specific examples of dimer acid-derived monomers include bis(hydroxyethyl)dimerate dimethacrylate (BHED-DMA), dimer acid dimethacrylate (DADMA), dimer acid diol ethyl carbamate dimethacrylate (DANHDMA), dimer acid diol ethyl carbonate dimethacrylate (DAHEMA), bis(hydroxypropoxy)dimerate dimethacrylate (BOHDDMA), dimer acid diisocyanate ethoxy dimethacrylate (HEMA/DDI), dimer acid diisocyanate phenoxypropoxy dimethacrylate(mono-BisGMA/DDI) and dimer acid diisocyanate BisGMA oligomer (oligomeric BisGMA/DDI) whose chemical structures are provided with the examples.

As used herein, a "monovinyl monomer" is a monomer having one polymerizable double bond per molecule. The monovinyl monomer may comprise any monomer which can be polymerized by a free-radical mechanism such as methacrylates and acrylates, styrene and derivatives thereof (styrenics), vinyl acetate, maleic anhydride, itaconic acid, N-alkyl (aryl) maleimides and N-vinyl pyrrolidone, vinyl pyridine, acrylamide, methacrylamide, N,N-dialkylmethacrylamides and acrylonitrile. Vinyl monomers, such as styrenics, acrylates and methacrylates, (meth)acrylamides and acrylonitrile are preferred monomers. Mixtures of more than one monovinyl monomer may be used.

Examples of suitable acrylate monomers include alkyl acrylates such as methyl acrylate and ethylacrylate (EA). Examples of suitable monovinyl (meth)acrylate monomers include $C_1$-$C_{20}$ alkyl(meth)acrylates, preferably $C_1$-$C_8$, and more preferably $C_1$-$C_4$, such as, for example, methyl(meth)acrylate, ethyl(meth)acrylate (EMA), propyl(meth)acrylate, n-butyl(meth)acrylate, iso-butyl(meth)acrylate, t-butyl (meth)acrylate, 2-ethylhexyl(meth)acrylate octyl (meth) acrylate and dodecyl(meth)acrylate.

As used herein, a "functional monomer" is a monomer having one or more reactive groups available for further polymerization. Such monomers include methacrylic acid and acrylic acid; (meth)acrylic anhydride, hydroxy alkyl acrylates such as hydroxy ethylacrylate (HEA); hydroxy alkyl methacrylates such as hydroxyethyl(meth)acrylate (HEMA), hydroxypropyl(meth)acrylate and hydroxybutyl (meth)acrylate, glycidyl (meth)acrylate, isocyanato(meth)acrylate such as isocyanatoethyl(meth)acrylate.

Unless otherwise specified or implied, the term "(meth) acrylate" includes both the methacrylate and the analogous acrylate.

As used herein, a "divinyl monomer" is a monomer having two polymerizable double bonds per molecule. Examples of suitable divinyl monomers include: ethylene glycoldi(meth) acrylate, tetraethyleneglycoldi(meth)acrylate (TEGDMA), the condensation product of bisphenol A and glycidyl methacrylate, 2,2'-bis[4-(3-methacryloxy-2-hydroxy propoxy)-phenyl] propane (bis-GMA), hexanediol di(meth)acrylate, tripropylene glycol di(meth)acrylate, butanediol di(meth) acrylate, neopentyl glycol di(meth)acrylate, diethylene glycol di(meth)acrylate, triethylene glycol di(meth)acrylate, dipropylene glycol di(meth)acrylate, allyl (meth)acrylate, divinyl benzene and derivatives thereof. Optionally, the divinyl monomer may comprise a mixture of more than one divinyl compound.

As used herein, a "monomer" may also include a reactive oligomer or reactive polymer or pre-polymer having at least one, but normally two or more, double bond per oligomers molecule which are polymerizable via a free-radical mechanism as the, or one of the, divinyl monomers. Examples of reactive oligomers include, but are not limited to, epoxy-(meth)acrylates, polyether(meth)acrylates, polyester-(meth) acrylates and urethane-(meth)acrylates. Examples of reactive polymers include addition or condensation polymers such as a styrene or acrylic copolymers containing pendant polymerizable (meth)acrylate groups or unsaturated polyesters. The molecular weight range of the oligomer or reactive polymer may vary from 500-500,000 g/mole.

A dimer acid-derived dimethacrylate dental restorative composition in accordance with an embodiment of the present invention is a mixture of one or more monomers, which may also include various fillers, initiators and accelerators as necessary for the application. Embodiments include compositions in which the mixture includes only one monomer, that monomer being a dimer acid-derived monomer, such as a dimer acid-derived dimethacrylate monomer of the structure shown in FIG. 2 wherein R is the same as R' and has one polymerizable double bond. The amount of total dimer acid-derived monomer can vary widely depending on the intended use, being about 0.1 wt % to about 100 wt %, based on the total weight of the composition. Preferably, embodiments have about 1 wt % to about 99 wt % based on the total weight of the composition. Alternative embodiments include comonomer systems having two or more monomers in a polymerizable mixture in which at least one monomer is a dimer acid-derived dimethacrylate monomer. In comonomer system embodiments, the amount of total dimer acid-derived monomers relative to the total weight of the monomers can vary widely depending on the intended use, from about 0.1 wt % dimer acid-derived monomer to about 100 wt % dimer acid-derived monomers (i.e., substantially of the monomers being dimer acid-derived monomers). Some alternative embodiments may also phase separate before or during polymerization as discussed later in this specification.

As briefly described above, dimer acid-derived dimethacrylate systems may also include and/or utilize various initiators, fillers, and accelerators depending on the application as discussed in greater detail below. For example, if photopolymerization using visible light is desired, camphorquinone may be used as an initiator. Alternatively, if ultraviolet photopolymerization is desired, then 2,2-dimethoxy-2-phenylacetophenone (DMPA) may be used as an initiator. Amine accelerators may also be used, as well as other accelerators.

Embodiments of the dimer acid-derived dimethacrylates systems of the present invention have some significant and unique advantages compared with (meth)acrylate polymerizations, that make the dimer acid-derived dimethacrylate systems extremely beneficial for dental resin applications. These advantages include: high conversion, which provides reduced leachable materials and improved stability to the polymeric network; a hydrophobic polymer structure that resists water uptake; low polymerization shrinkage; and the potential for controlled phase separation during copolymerizations. For example, as shown in TABLE 1, a comonomer system of about 70 wt % EBPADMA, about 20 wt % BOHD-DMA and about 10 wt % UDMA exhibited greater than 80% conversion, and a shrinkage stress that was almost 35% less than that of a typical dental restorative based on a 70/30 wt % BisGMA/TEGMA system.

In some comonomer embodiments (i.e., embodiments wherein a mixture of two monomers is used), phase separation between the monomers was observed and determined to be a factor in the properties of the resulting polymerized resin system. The bis(hydroxyethyl)dimerate dimethacrylate (BHEDDMA; see structures in FIG. 1) forms a stable phase-separated monomeric mixture with urethane dimethacrylate (UDMA) and a gross phase separation with Bis-GMA. This incompatibility results from the very non-polar, hydrophobic structure of BHEDDMA, which has very limited hydrogen bonding interactions with UDMA and Bis-GMA monomers. However, BHEDDMA forms homogeneous resin compositions with ethoxylated bisphenol A dimethacrylate (EB-PADMA) or other monomers that do not have significant hydrogen bonding interactions. When polymerized as a diluent comonomer with EBPADMA, BHEDDMA provides resins with high conversion, excellent mechanical properties, increased work of fracture (a measure of toughness) and lower water sorption compared with an analogous EBPADMA/TEGDMA resin. While BHEDDMA exhibits low shrinkage as a homopolymer, comonomer systems that include BHEDDMA exhibit extremely low shrinkage (only 25 to 50% of the shrinkage expected based on the actual conversion) and low shrinkage stress. We believe that the micro-phase separation that occurs during polymerization accounts for the low shrinkage and the resulting heterogeneous polymer morphology can also account for the reduced stress and enhanced toughness.

The onset and extent of the micro-phase separation can be controlled based on the proportions of comonomers in the resin, interactions (particularly hydrogen-bonding interactions) between the monomers and additional parameters such as polymerization rate and cure temperature. The specific chemical functionality used in the connecting group between the dimer acid core and the methacrylate polymerizable groups can be used to controllably alter the compatibility of the dimer acid-derived monomer with other comonomers. This compatibility match or mismatch is then used to control the potential for phase separation either before or during the polymerization. In compositions of two monomers, one of which is the dimer acid-derived dimethacrylate, the monomer compatibility and comonomer ratio can be used to control the phase separation process. Greater control over phase separation can be achieved if three (or more) comonomers are used where the dimer acid-derived dimethacrylate is compatible with one comonomer but incompatible with the other (as with the example previously mentioned for the BHEDDMA/UDMA/EBPADMA ternary composition). The phase separation process must be managed such that the domain size remains small (micro-phase separation) so that the optical clarity of the polymer is not dramatically altered. This is important for both the photopolymerization efficiency and the esthetic appearance of the final polymer.

Some of the dimer acid-based monomers that have been developed are shown in FIG. 1 and others are presented with the examples. In addition to these monomers, commercially available diisocyanate derivatives of dimer acid may be used as a starting material to prepare the urethane dimethacrylate isomer of monomer DANHDMA (in FIG. 1) in a single simple condensation step with HEMA or other hydroxy-functionalized (meth)acrylate. BHEDDMA and DADMA have relatively low viscosities and phase separate from Bis-GMA or UDMA in the monomeric state.

The amount of total filler component in the dental composition can vary widely depending on the intended use, being about 1 wt % to about 90 wt %, based on the total weight of the dental restorative composition. The amount of filler component used may be determined by the requirements of the particular application. Thus, for example, cavity filling materials generally comprise about 60 to about 90 wt % filler; luting cements comprise about 20 to about 80 wt % filler; sealants generally comprise about 1 to about 20 wt % filler; adhesives generally comprise about 1 to about 30 wt % filler; and restoratives comprise about 50 to about 90 wt % filler, with the remainder in all cases being the other components of the dental composition.

In addition to the above monomers and oligomers, the dental resin composition also includes a curing system, comprising polymerization initiators, polymerization accelerators, and/or the like. Suitable polymerization initiators include initiators known in the art. For example, visible light curable compositions employ light-sensitive compounds including but not being limited to benzil, benzoin, benzoin methyl ether, DL-camphorquinone, benzil diketones and acylphosphine oxides. Either UV-activated cure or visible light-activated cure (approximately 230 to 750 nm) is acceptable. The amount of photoinitiator is selected according to the curing rate desired. A minimally catalytically effective amount is generally about 0.01 wt %, based on the total weight of the curable organic component, and will lead to a slower cure. Faster rates of cure may be achieved with amounts of catalyst of greater than or equal to about 0.01 wt % to about 5 wt %, based on the total weight of the curable monomer.

Alternatively, the composition may be formulated to be self-curing. Self-curing compositions will generally contain free radical polymerization initiators such as, for example, a peroxide in an amount of about 0.05 to about 4.0 wt % of the total weight of the curable monomer mixture. Preferred free radical initiators include lauryl peroxide, tributyl hydroperoxide, and the like, with a benzoyl peroxide being more preferred. Other reducing agents suitable for self-cure polymerization initiations are salts of sulfinic acid, for example, the sodium salt of benzenesulfinic acid.

Polymerization accelerators suitable for use include various organic tertiary amines well known in the art. In visible light curable compositions, for example, tertiary amines are generally acrylate derivatives, such as dimethylaminoethyl methacrylate and, particularly, diethylaminoethyl methacrylate (DEAEMA) in an amount of about 0.05 to about 0.5 wt %. In the self-curing compositions, the tertiary amines are generally aromatic tertiary amines, preferably tertiary aromatic amines such as ethyl 4-(dimethylamino)benzoate (EDMAB), 2-[4-(dimethylamino)phenyl]ethanol, N,N-dimethyl-p-toluidine (DMPT), bis(hydroxyethyl)-p-toluidine, and triethanolamine. Such accelerators are generally present at about 0.1 to about 4.0 wt % based on the total weight of the curable resin component.

Other additives may also be present in the dental resin composition, including, for example, ultraviolet light absorbers, antioxidants, and other additives well known in the art. It is preferred to employ an ultraviolet absorber at about 0.05 to about 5.0 wt %, based on the total weight of the dental composition. Such UV absorbers are particularly desirable in the visible light curable compositions in order to avoid discoloration of the resin from any incident ultraviolet light. Suitable UV absorbers include, for example, various benzophenones, particularly UV-5411 available from American Cyanamid Company.

The above described dental composition may be provided to the practitioner in the form a single composition, wherein the curing reaction may be triggered shortly before usage in dental restorative applications by the utilization of, for example, visible light, UV light and/or increased temperature. When formulated as a one-part composition, preferably, the single admixture does not separate during normal storage.

Alternatively, the components may be provided to the practitioner as a multiple-component composition wherein two or more component combinations are mixed just prior to use. Examples of multiple component compositions include, for example, one component combination including a first dimer acid-derived monomer and the other component combination including a diluent acrylate or methacrylate monomer, a reactive glass, an initiator, an accelerator, and the like. A preferred two-part formulation provides the liquid components (e.g., curable organic components and water, if any) as one part, and the dry components (e.g., fillers and initiators) as a second part. In an especially preferred embodiment, a composition is formulated to provide UV and/or visible light curing together with self-curing. Such compositions are most conveniently provided to the practitioner in two parts.

In use, the compositions are provided to the practitioner who applies them to the appliance or to the site to be restored by methods known in the art. After application, the compositions are cured, either through a self-cure process, exposure to UV and/or visible light, or a combination thereof.

In addition to dimer acid-derived monomers, embodiments of the present invention include certain novel "bulky" monomers described in the Examples section. These bulky monomers were developed to provide high molecular weight, low shrinkage comonomers for use with the dimer acid-derived monomers. The bulky monomers are of an increased size when compared to the typical diluents and are effective in further reducing the shrinkage stress of cured systems as shown in Table 1.

EXAMPLES

Example 1

Synthesis of Dimer Acid-Derived Monomers—General Methods

In preparation of dimer acid-derived monomers, a dimer acid hydrogentate was used as a starting material, and converted to the diol (1).

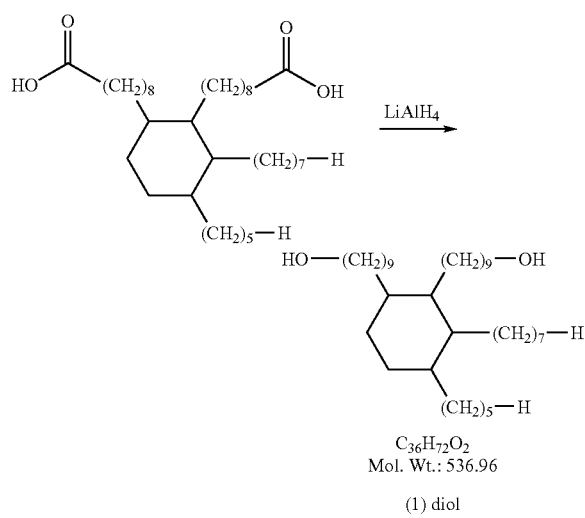

$C_{36}H_{72}O_2$
Mol. Wt.: 536.96

(1) diol

Ten (10) g (0.0177 mol) of dimer acid hydrogenate dissolved in 200 mL of ethyl ether was added slowly, at room temperature under nitrogen atmosphere to an excess of LiAlH$_4$ suspended in 200 mL of ethyl ether. The reaction mixture was then refluxed for 1 hour and then stirred at room temperature over night. Two hundred (200) mL of cooled water was added carefully followed by addition of a 10% solution of sulfuric acid to neutralize the unreacted LiAlH$_4$. The organic layer was separated and the aqueous layer washed three times with ether. The organic layers were collected and dried with Na$_2$SO$_4$. Finally, the solvent was evaporated to obtain 6.9039 g (73%) of colorless viscous oil. The IR, $^1$H NMR and $^{13}$C NMR were recorded.

IR (KBr, cm$^{-1}$): ν 3327 (OH), 2926, 2854 (CHaliphatic)
$^1$H NMR (500 MHz, CDCl$_3$): δ 3.62 (m, OCH$_2$), 2.09 (s, 2H, OH), 1.9-1.0 (m, CH and CH$_2$), 0.88 (m, CH$_3$).
$^{13}$C {$^1$H} NMR (125 MHz, CDCl$_3$): δ 62.8 (OCH$_2$), from 35 to 22 (CH and CH$_2$ aliphatic), 14.0 (CH$_3$).

Example 2

Synthesis of DADMA (2)

DADMA
$C_{44}H_{80}O_4$
Mol. Wt.: 673.10

1.6991 g (0.00316 mol) of diol (1) dissolved in 50 mL of methylene chloride and 0.6715 g (0.0066 mol; 2.1 eq) of triethyl amine were mixed under nitrogen atmosphere. 0.6615 g (0.00632 mol, 2 eq) of methacryloyl chloride in 20 mL of CH$_2$Cl$_2$ was added to the mixture drop-wise. The reaction was allowed to stir for 18 hours at room temperature. The reaction mixture was then treated with 1M solution of HCl (2×20 mL), a concentrated solution of NaHCO$_3$ (2×20 mL) and finally with water (1×10 mL). The organic layer was dried with Na$_2$SO$_4$ and the solvent was evaporated to obtain a liquid in 60% yield.

IR (KBr, cm$^{-1}$): ν 3105 (=CH$_2$), 2925, 2854 (CHaliphatic), 1721 (CO), 1639 (=CH$_2$)
$^1$H NMR (500 MHz, CDCl$_3$): δ 6.04, 5.48 (m, =CH$_2$), 4.09 (m, OCH$_2$), 1.89 (s, CH$_3$), 1.9-1.0 (m, CH and CH$_2$), 0.83 (m, CH$_3$).
$^{13}$C {$^1$H} NMR (125 MHz, CDCl$_3$): δ 167.6 (CO), 136.7 (C=CH$_2$), 125.2 (C=CH$_2$), 64.9 (OCH$_2$), from 38 to 20 (CH and CH$_2$ aliphatic), 18.5 (CH$_3$), 14.3 (CH$_3$).

Example 3

Synthesis of DANHDMA (3)

DANHDMA
$C_{50}H_{90}N_2O_8$
Mol. Wt.: 847.26

To a solution of 4.0623 g of diol (1) in 50 mL of CH$_2$Cl$_2$ and 1.6077 g (0.0589 mol, 2.1 eq) of NEt$_3$, 2.3479 g (0.01513 mol, 2.0 eq) of isocyanate ethylmethacrylate was added dropwise under nitrogen atmosphere at room temperature. The reaction mixture was stirred over night to warranty complete reaction. The reaction mixture was then treated with HCl (1M solution, 2×10 mL), NaHCO$_3$ (saturated solution 2×0 mL) and water (1×10 mL). The organic layer was separated and dried with Na$_2$SO$_4$, filtered and purified by chromatographic column using a mixture CH$_2$CL$_2$:Ethyl acetate 80:20 to obtain 5.215 g (yield 82%) of colorless oil.

IR (KBr, cm$^{-1}$): ν 3357 (NH), 3104 (=CH$_2$), 2925, 2854 (CHaliphatic), 2270 (OCN), 1722 (CO), 1639 (=CH$_2$)

$^1$H NMR (500 MHz, CDCl$_3$): δ 6.11, 5.57 (m, =CH$_2$), 4.99 (s-br, NH), 4.21, 4.03 (m, OCH$_2$), 3.47 (NHCH$_2$), 1.93 (s, CH$_3$), 1.9-1.0 (m, CH and CH$_2$), 0.87 (m, CH$_3$).

$^{13}$C {$^1$H} NMR (125 MHz, CDCl$_3$): δ 167.4, 156.9 (CO), 136.2 (C=CH$_2$), 126.1 (C=CH$_2$), 65.4 (NCH$_2$), 63.9 (OCH$_2$), from 40 to 20 (CH and CH$_2$ aliphatic), 18.4 (CH$_3$), 14.2 (CH$_3$).

Example 4

Synthesis of Acyl-Chloride Intermediate

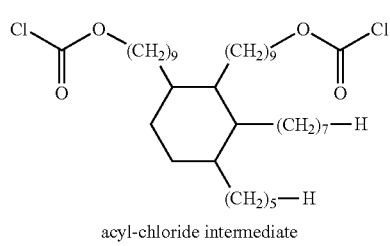

(4)

acyl-chloride intermediate
C$_{38}$H$_{70}$Cl$_2$O$_4$
Mol. Wt.: 661.87

3.0709 g (0.0057 mol) of diol (1) was dissolved in 80 mL of methylene chloride under nitrogen atmosphere and mixed with triethyl amine (1.1555 g, 0.0114 mol, 2.1 eq). One (1) mL (1.4290 g, 0.0112 mol) of oxalyl chloride dissolved in 10 mL of CH$_2$Cl$_2$ was added. Once the addition started, the reaction mixture turned dark yellow and evidence of gas formation was shown in the bubble oil reservoir. Upon completion of the addition, the reaction mixture is light yellow. Stirring was continued until the next day. The reaction mixture was then treated with 1M solution of HCL (2×50 mL), NaHCO$_3$ (2×50 mL) and 30 mL of water. The organic layer was dried with Na$_2$SO$_4$ and the solvent was removed to obtain a viscous yellow material. The new compound was purified by chromatographic column using a mixture 90:10 of methylene chloride:ethyl acetate (yield 67%).

IR (KBr, cm$^{-1}$): ν 2925, 2854 (CHaliphatic), 1768, 1744 (CO), 740 (C—Cl)

$^1$H NMR (500 MHz, CDCl$_3$): δ 4.28 (m, OCH$_2$), 1.8-1.0 (m, CH and CH$_2$), 0.89 (m, CH$_3$).

$^{13}$C {$^1$H} NMR (125 MHz, CDCl$_3$): δ 158.0 (CO), 67.1 (OCH$_2$), from 35 to 22 (CH and CH$_2$ aliphatic), 14.1 (CH$_3$)

Example 5

Synthesis of DAHEMA

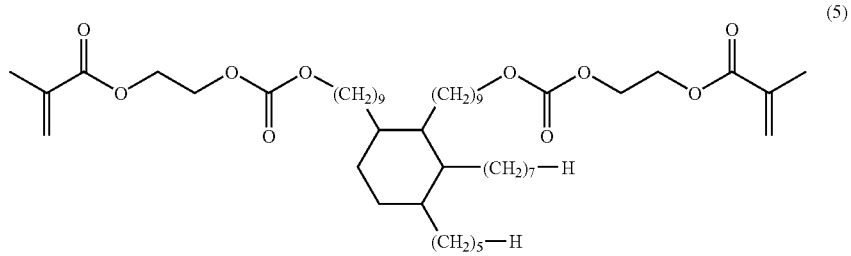

(5)

DAHEMA
C$_{50}$H$_{88}$O$_{10}$
Mol. Wt.: 849.23

A solution of acyl-chloride (4) 1.3415 g (0.020 mol) in 20 mL of $CH_2Cl_2$ was added drop-wise to a mixture of hydroxy-etheyl methacrylate (HEMA) 0.5275 g (0.0040 mol) and 0.04250 g (0.0042 mol) of $NEt_3$ in 20 mL of $CH_2Cl_2$ at room temperature. The reaction mixture was stirred for 18 hours followed by washing with 1 M solution of HCl (2×10 mL), $NaHCO_3$ (2×10 mL) and finally with water (2×5 mL). The organic layer was dried ($Na_2SO_4$), filtered and the solvent was evaporated. TLC showed 2 spots which were separated using a mixture 80:20 $CH_2CL_2$: ethyl acetate. The first fraction collected corresponded to un-reacted acyl-chloride and the second fraction was the expected product (DAHEMA), which was obtained as colorless oil in 45% of yield.

IR (KBr, $cm^{-1}$): ν 2925, 2854 (CHaliphatic), 1768, 1744, 1722 (CO), 1639 (=$CH_2$)

$^1$H NMR (500 MHz, $CDCl_3$): δ 6.16, 5.62 (m, =$CH_2$), 4.31, 3.89, 3.65 (m, $OCH_2$), 1.97 (M, $CH_3$), 1.8-1.0 (m, CH and $CH_2$), 0.88 (m, $CH_3$).

Example 6

Synthesis of BHEDDMA reduced pressure to obtain a light pink low viscosity product which was purified by chromatographic column eluted first with $CH_2Cl_2$ to remove a first fraction of impurity and then with ethyl acetate to obtain BHEDDMA as a colorless low viscous oil in a yield of 80%. Alternatively, BHEDDMA was also prepared by the analogous procedure with dimer acid diglycidyl ester (Aldrich) and methacrylic acid used as the starting materials.

IR (KBr, $cm^{-1}$): ν 3105 (=$CH_2$), 2926, 2854 (CHaliphatic), 1742, (CO), 1639 (=$CH_2$)

$^1$H NMR (500 MHz, $CDCl_3$): δ 6.09, 5.55 (m, =$CH_2$), 4.37, 3.31, 4.24 (m, OCH and $OCH_2$), 2.25 (m, $CH_2$), 1.92 (M, $CH_3$), 1.8-1.0 (m, CH and $CH_2$), 0.85 (m, $CH_3$).

$^{13}C\{^1H\}$ NMR (125 MHz, $CDCl_3$): δ 173.6, 167.1 (CO), 136.1 ($\underline{C}H$=$CH_2$), 126.0 (CH=$\underline{C}H_2$), 62.6, 62.4, 62.1, 61.9

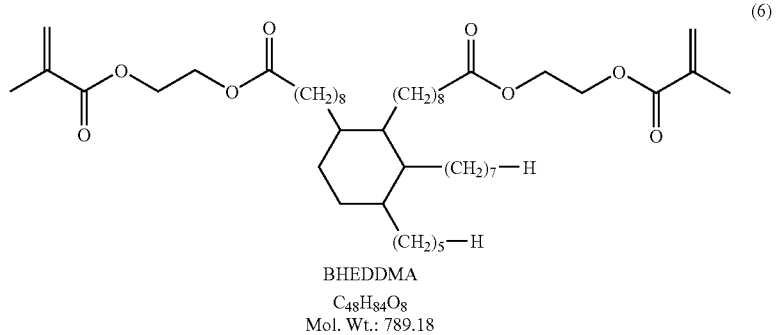

(6)

BHEDDMA
$C_{48}H_{84}O_8$
Mol. Wt.: 789.18

0.6 mL of methacryloyl chloride dissolved in 15 mL of $CH_2CL_2$ was added drop-wise to a mixture of 2.0 g (3.04 mmol) bis(hydroxyethyl)dimerate (Emery 9360A) and 0.66 g (6.5 mmol, 0.9 mL) $NEt_3$ under nitrogen atmosphere at −5° C. with stirring. After completion of the addition, the reaction mixture was allowed to reach room temperature and was stirred for 5 hours. The IR at this stage showed complete ($OCH_2$ and OCH), from 34 to 22 (CH and $CH_2$ aliphatic), 18.3 ($CH_3$), 14.2 ($CH_3$)

Example 7

Synthesis of BOHDDMA

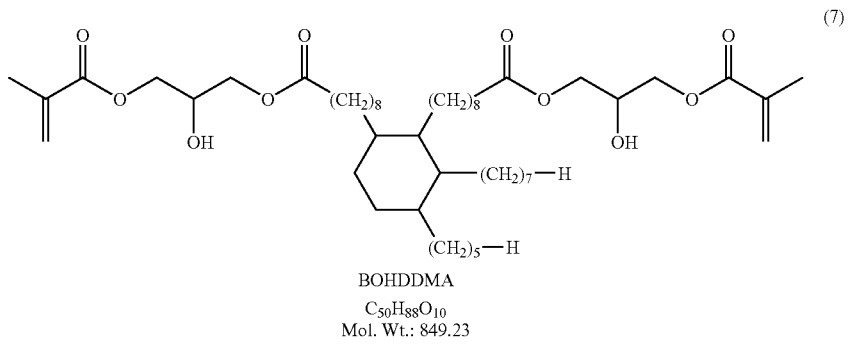

(7)

BOHDDMA
$C_{50}H_{88}O_{10}$
Mol. Wt.: 849.23 disappearance of the alcohol peak. The reaction mixture was treated with dilute HCL (1 M), followed by extraction with $NaHCO_3$ and water. The solvent was evaporated under 8.19 g (14.37 mmol) hydrogenated dimer acid was mixed with 4.023 g (28.33 mmol) of glycidyl methacrylate and 0.068 g triphenylphosphine used as a catalyst. The reaction mixture was heated at 90° C. under nitrogen atmosphere overnight. ¹H NMR indicated the presence of two isomers in a ratio of 75:25. 7.7 g (yield 65%) of product was obtained using a chromatographic column. Methylene chloride:ethyl acetate in a 60:40 proportion was used as eluent. A brown slightly viscous liquid was obtained after evaporation of solvents.

IR (KBr, cm⁻¹): ν 3473 (OH), 3103 (=CH₂), 2925, 2854 (CHaliphatic), 1724 (CO), 1638 (=CH₂)

¹H NMR (500 MHz, CDCl₃): δ 6.12, 5.59 (m, =CH₂), 5.15 (t, CHminority isomer), 4.33 (m, CHO), 4.19, 3.75 (m, OCH₂), 2.45 (s-br, OH), 2.25 (m, CH₂), 1.97 (m, CH₃), 1.8-1.0 (m, CH and CH₂), 0.88 (m, CH₃).

¹³C {¹H} NMR (125 MHz, CDCl₃): δ 174.0, 167.4 (CO), 136.0 (CH=CH₂), 126.3 (CH=CH₂), 72.2, 68.1, 65.2, 62.9, 61.3 (OCH₂ and OCH), from 35 to 22 (CH and CH₂ aliphatic), 18.4 (CH₃), 14.2 (CH₃)

Example 8

Synthesis of HEMA/DDI

HEMA/DDI
C₅₀H₉₀N₂O₈
Mol. Wt.: 847.26

A mixture of 3.0 g of HEMA (0.0230 mol), 6.4712 g of DDI (0.0110 mol) and 0.0775 g of dibutyltin diluarate (0.0001 mol) (which is 1.1% based on the moles of DDI) was heated at 40° C. The mixture was initially immiscible, but became miscible very readily on stirring at 40° C. IR measurement after 3 hours showed complete disappearance of the isocyanate peak.

IR (KBr, cm⁻¹): ν 3351 (NH), 1723 (CO), 1636 (=CH₂)

¹H NMR (270 MHz, CDCl₃): δ 6.11, 5.59 (s, =CH₂), 4.74 (s-br, NH), 4.32 (s-br, NHCH₂), 3.16 (m, OCH₂), 1.96 (M, CH₃), 1.9-1.0 (m, CH and CH₂), 0.88 (m, CH₃)

¹³C {¹H} NMR (68.1 MHz, CDCl₃): δ 166.9, 156.0 (CO), 135.9 (C=CH₂), 125.7 (C=CH₂), 62.9 (NCH₂), 62.3 (OCH₂), from 41 to 22 (CH and CH2 aliphatic), 18.1 (CH₃), 14.0 (CH₃).

Example 9

Synthesis of Mono-BisGMA

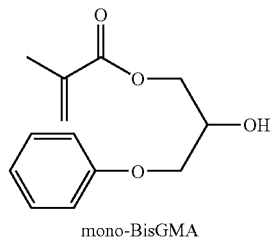

mono-BisGMA

-continued

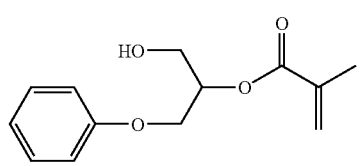

7.5832 g (0.0500 mol) of 1,2-epoxy-3-phenoxypropane (EPP), 4.3826 g (0.0500 mol) of methacylic acid, 0.1 g triphenylphosphine and trace amount of 2,6 Di-t-butyl-4-methylphenol (BHT) were transferred into a vial. The sealed vial was heated at 93° C. for 19 h and then brought to room temperature. A ¹H NMR recorded at this stage showed no peak due to EPP compound. The residue was passed through a small pad of silica gel with the aid of 75 mL of ethyl acetate. Solvent was removed under vacuum and the residue passed through a 0.2 μm filter which gave clear but slightly off colored liquid. A mixture of two isomers was obtained.

IR (KBr, cm⁻¹): ν 3460 (OH), 1717 (CO), 1636, 1600 (=CH₂)

$^1$H NMR (270 MHz, CDCl$_3$): δ 7.29, 6.93 (m, CH aromatic), 6.15, 5.60 (s, =CH$_2$), 5.26, 4.35 (m, CH), 4.28, 4.20, 4.09 (m, OCH$_2$), 2.91 (s-br, OH), 1.95 (s, CH$_3$).

$^{13}$C {$^1$H} NMR (68.1 MHz, CDCl$_3$): δ 167.4 (CO), 158.3 (C aromatic), 135.8 (C=CH$_2$), 129.5, 121.3, 114.5, 113.2 (CH aromatic), 126.2 (C=CH$_2$), 68.6, 66.2, 65.5, 61.9 (OCH$_2$), 73.3, 68.6 (OCH), 18.2 (CH$_3$)

Example 10

Synthesis of Mono-BisGMA/DDI

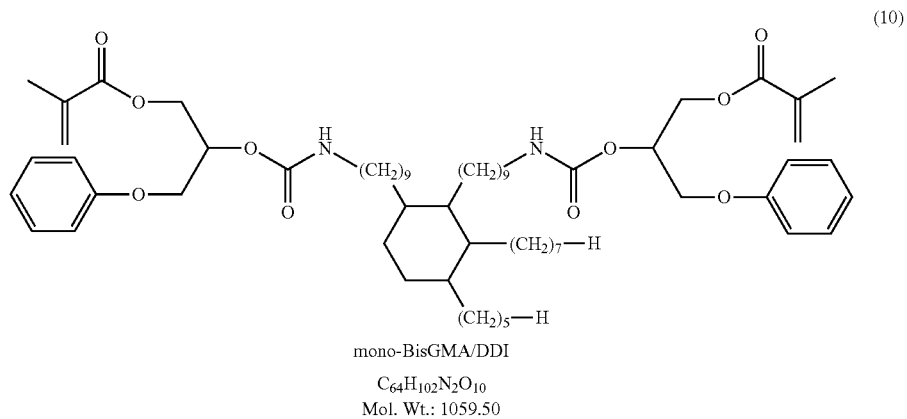

mono-BisGMA/DDI
C$_{64}$H$_{102}$N$_2$O$_{10}$
Mol. Wt.: 1059.50

5.9657 g of mono-BisGMA (9), 7.4423 g (0.1268 mol) of isocyanate derived from dimer acid (DDI) and 0.0923 g (0.000146 mol) of dibutyl dilaurate were heated at 55° C. until the isocyanate peak disappeared completely (18 h). The reaction mixture was filtered through a small silica gel with dichloromethane. The solvent was removed under reduced pressure to provide (10) as a pale yellow viscous oil.

IR (KBr, cm$^{-1}$): ν 3360 (NH), 1721 (CO), 1639 (=CH$_2$)

$^1$H NMR (270 MHz, CDCl$_3$): δ 7.28, 6.93 (m, CH aromatic), 6.12, 5.58 (s, =CH$_2$), 5.33 (m, CH), 4.77 (s-br, NH), 4.44, 4.16 (m, OHCH$_2$), 3.16 (m, NHCH$_2$), 1.4-1.20 (m, CH and CH$_2$), 1.94 (s, CH$_3$), 0.87 (m, CH$_3$).

$^{13}$C {$^1$H} NMR (68.1 MHz, CDCl$_3$): δ 169.9, 155.5 (CO), 158.4 (Caromatic), 135.9 (C=CH$_2$), 129.5, 121.3, 114.7, 114.6 (CH aromatic), 126.0 (C=CH$_2$), 70.1 (OCH), 68.7, 66.5, 66.1, 63.2 (OCH$_2$), 41.3 (NHCH$_2$), from 30 to 20 (CH and CH$_2$), 18.2 (CH$_3$), 12.7 (CH$_3$)

Example 11

Synthesis of Oligomeric BisGMA/DDI

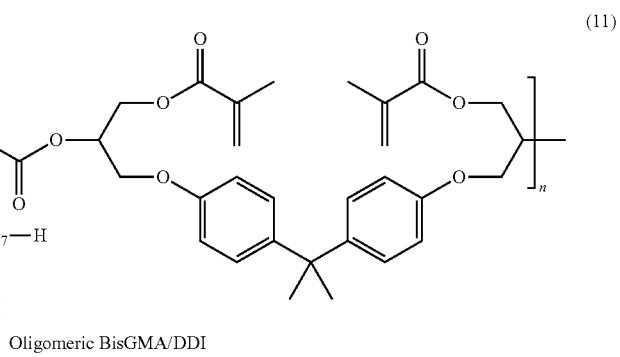

Oligomeric BisGMA/DDI 15.44 g of BisGMA (0.031 mol) and 0.1 g of dibutyl dilaurate were transferred into a 100 mL flask with stir bar with 50 mL of dry methylene chloride. After complete dissolution of BisGMA into methylene chloride, 18 g of DDI (0.0305 mol) in 15 mL of methylene chloride was added with stirring. The flask was stoppered and allowed to stir for 11 days. The crude reaction mixture was concentrated to approximately half its original volume and added drop-wise to methanol to precipitate the oligomeric product. The solvent was decanted and the precipitate was dried under vacuum at 40° C. The urethane oligomer (11) was obtained as an extremely viscous, pale yellow liquid.

IR (KBr, cm$^{-1}$): ν 3485 (NH), 1720 (CO), 1639, 1606 (=CH$_2$)

$^1$H NMR (270 MHz, CDCl$_3$): δ 7.10, 6.80 (m, CH aromatic), 6.11, 5.59 (s, =CH$_2$), 4.32-3.21 (m, CH and CH$_2$), 1.94, 1.60, 1.22, 0.85 (CH$_3$).

$^{13}$C {$^1$H} NMR (68.1 MHz, CDCl$_3$): δ 167.8, 156.34, 143.6, 136.0, 128.1, 126.1, 114.1, 68.6, 65.4, 63.2, 53.3, 41.6, 40.7, 31.9, 31.1, 29.71, 26.7, 22.79, 18.2, 14.1

Example 12

Synthesis of Comonomers—General Methods

The general procedure used for the synthesis of bulky dimethacrylate monomers involved the ring opening of a diepoxide with the corresponding aromatic alcohol using triphenylphospine as catalyst (1.5% base on the diepoxy), followed by conversion of the resulting diol to the dimethacrylate using methacrylic anhydride in the presence of dimethylamino pyridine as catalyst (mole fraction of catalyst 2% base on diol). Typical reaction procedures are described below:

A mixture of bisphenol A diglycidyl ether 10.0254 g (30 mmol), 12.76054 g (62.1 mmol) of 3,5 di-tert-butyl phenol and 0.1153 g of triphenylphosphine was stirred at 85° C. for 18 hours under nitrogen atmosphere. After cooling the reaction mixture, the excess of 3,5-di-tert-butyl phenol was removed by sublimation under vacuum. The light brown residue obtained was diluted in CH$_2$Cl$_2$ and purified by chromatographic on a silica gel column (5×25 cm) with a mixture 90:10/CH$_2$Cl$_2$: Ethyl acetate. The product (12), a light yellow solid, was obtained in 86% yield (20.4802 g) after removing the solvents under reduced pressure.

IR (KBr, cm$^{-1}$): ν 3391 (OH), 3052 (CH$_{aromatic}$), 29652-2870 (CH$_{aliphatic}$), 1605-1592 (C=C$_{aromatic}$)

$^1$H NMR (500 MHz, CDCl$_3$): δ 7.19, 6.89 (d, $^3$J(H—H)=8.8 Hz, each 2H, each CHPh), 7.10 (t, $^4$J(H—H)=1.6 Hz, 1H, CHPh), 6.84 (d, $^4$J(H—H)=1.6 Hz, 2H, CHPh), 4.43 (m, 1H, CH), 4.20 (m, 4H, CH$_2$O), 2.78 (s, 1H, OH), 1.68 (s, 3H, CH$_3$), 1.36 (s, 18H, CH$_3$)

$^{13}$C {$^1$H} NMR (125 MHz, CDCl$_3$): δ 158.2, 156.5, 152.5, 143.9 (CPh), 128.0, 115.7, 114.2, 109.1 (CHPh), 69.1, 68.9 (CH$_2$), 68.8 (CH), 41.9 (C), 34.2 (CBu$^t$), 31.6 (CH$_3$Bu$^t$), 31.2 (CH$_3$)

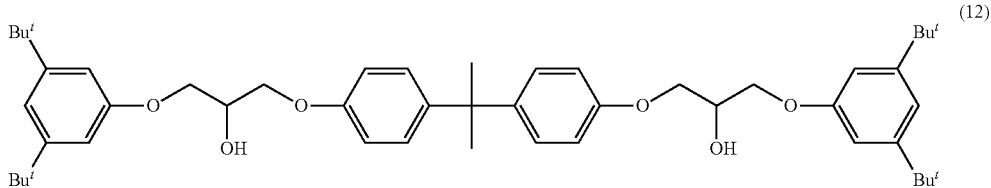

Example 13

D$^t$BDMA-Bisphenol A

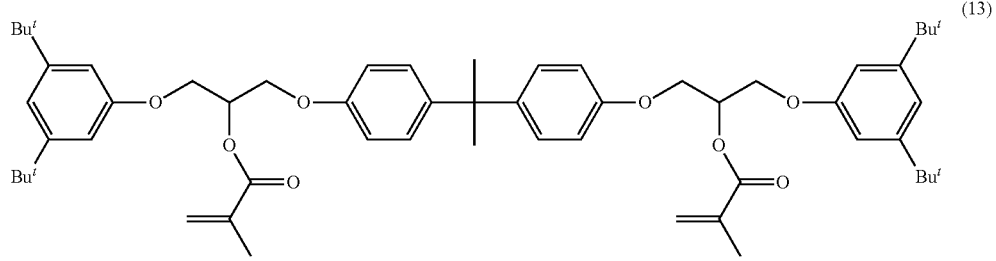

D$^t$BDMA-Bisphenol A 17.3184 g (23 mmol) of 6 were dissolved in 180 mL of $CH_2Cl_2$. Then 4.6547 g (46 mmol) of $NEt_3$ and 0.056 g (0.46 mmol) of dimethylaminopyridine (DMPA) were added under nitrogen atmosphere. The mixture was cooled at 0° C. and 7.0963 g (46 mmol) of methacrylic anhydride dissolved in 40 mL of $CH_2CL_2$ were added drop wise and the reaction mixture was stirred at room temperature until next day. The mixture was treated with HCL (1 M solution) 3×50 mL, $NaHCO_3$ (3×50 mL) and then with distilled water 2×30 mL. The organic layer was dried with $NaSO_4$, filtered and the solvent was removed under vacuum. The compound was purified by chromatographic column using $CH_2Cl_2$ as eluent. After removal the solvent 17.3208 g of colorless very viscous oil were obtained (91% yield).

IR (KBr, cm$^{-1}$): ν 3103 (=$CH_2$), 3052, 3038 ($CH_{aromatic}$), 2964, 2869 ($CH_{aliphatic}$), 1721 (CO), 1637 (=$CH_2$), 1605, 1592 (C=$C_{aromatic}$)

$^1$H NMR (500 MHz, $CDCl_3$): δ 7.19, 6.88 (d, $^3J(H-H)$=8.8 Hz, each 2H, each CHPh), 7.09 (t, $^4J(H-H)$=1.7 Hz, 1H, CHPh), 6.84 (d, $^4J(H-H)$=1.7 Hz, 2H, CHPh), 6.19, 5.60 (m, each 1H, =$CH_2$), 5.58 (m, 1H, CH), 4.20 (m, 4H, $CH_2O$), 1.98 (s, 3H, $CH_3$), 1.68 (s, 3H, $CH_3$), 1.36 (s, 18H, $CH_3$)

$^{13}C\{^1H\}$ NMR (125 MHz, $CDCl_3$): δ 166.9 (CO), 158.3, 156.5, 152.5, 143.8 (CPh), 136.1 (C=$CH_2$), 127.9, 115.6, 114.3, 109.3 (CHPh), 126.6 (C=$\overline{C}H_2$), 71.3 (CH), 66.2 ($CH_2O$), 41.9 (C), 35.1 ($CBu^t$), 31.$\overline{6}$ ($CH_3Bu^t$), 31.5, 18.4 ($CH_3$).

Example 14

Compound 14

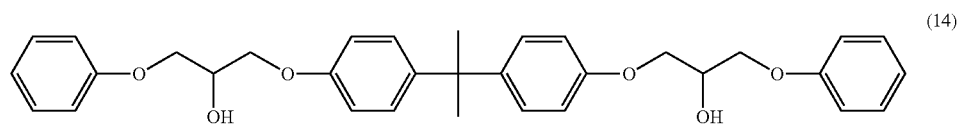 [SMILES: CC(C)(c1ccc(OCC(O)COc2ccccc2)cc1)c1ccc(OCC(O)COc2ccccc2)cc1]

(14)

IR (KBr, cm$^{-1}$): ν 3415 (OH), 3360, 3039 ($CH_{aromatic}$), 2965, 2933, 2874 ($CH_{aliphatic}$), 1599, 1587 (C=$C_{aromatic}$)

$^1$H NMR (500 MHz, $CDCl_3$): δ 7.31 (t, $^3J(H-H)$=8.5 Hz, each 2H, CHPh), 7.00 (t, $^3J(H-H)$=7.4 Hz, 1H, CHPh), 6.95 (d, $^3J(H-H)$=8.5 Hz, each 2H, CHPh), 7.16, 6.86 (d, $^3J(H-H)$=8.8 Hz, each 2H, CHPh), 4.40 (m, 1H, CH), 4.17 (m, 4H, $CH_2O$), 3.00 (s-br, 1H, OH), 1.66 (s, 3H, $CH_3$)

$^{13}C\{^1H\}$ NMR (125 MHz, $CDCl_3$): δ 158.9, 156.7, 144.1 (CPh), 129.9, 128.2, 121.7, 115.0, 114.4 (CHPh), 69.3 ($CH_2O$), 69.1 (CHOH), 42.2 (C), 31.5 ($CH_3$)

Example 15

PhDMA-Bisphenol A

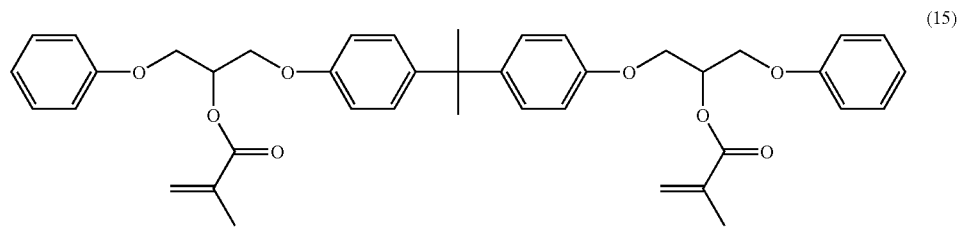

(15)

PhDMA-Bisphenol A

IR (KBr, cm$^{-1}$): ν 3101 (=$CH_2$), 3064, 3040 ($CH_{aromatic}$), 2965, 2931, 2875 ($CH_{aliphatic}$), 1719 (CO), 1637 (=$CH_2$), 1599, 1588 (C=$C_{aromatic}$)

$^1$H NMR (500 MHz, $CDCl_3$): δ 7.31 (t, $^3J(H-H)$=8.6 Hz, each 2H, CHPh), 6.99 (t, $^3J(H-H)$=7.1 Hz, 1H, CHPh), 6.95 (d, $^3J(H-H)$=8.6 Hz, each 2H, CHPh), 7.14, 6.84 (d, $^3J(H-H)$=8.8 Hz, each 2H, CHPh), 6.14, 5.60 (m, each 1H, =$CH_2$), 5.53 (m, 1H, CH), 4.15 (m, 4H, $CH_2O$), 1.95 (s, 3H, $CH_3$), 1.64 (s, 3H, $CH_3$)

$^{13}C\{^1H\}$ NMR (125 MHz, $CDCl_3$): δ 167.3 (CO), 158.9, 156.8, 144.1 (CPh), 136.3 (C=$CH_2$), 129.9, 128.2, 121.7, 115.2, 114.6 (CHPh), 126.2 (C=$\overline{C}H_2$), 71.3 (CHO), 69.1, ($CH_2O$), 42.2 (C), 31.5 ($CH_3$), 18.$\overline{7}$ ($CH_3$)

Example 16

M^tBuDMA-Bisphenol A

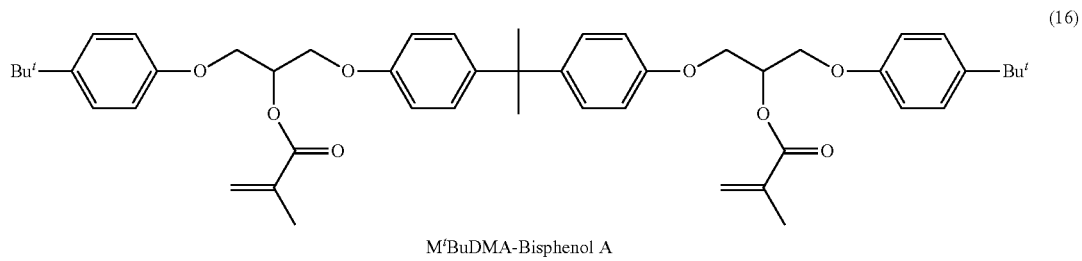

M^tBuDMA-Bisphenol A (16)

IR (KBr, cm$^{-1}$): ν 3103 (=CH$_2$), 3060, 3039 (CH$_{aromatic}$), 2963, 2870 (CH$_{aliphatic}$), 1720 (CO), 1637 (=CH$_2$), 1605–1592 (C=C$_{aromatic}$)

$^1$H NMR (500 MHz, CDCl$_3$): δ 7.32, 6.89 (d, $^3$J(H—H)= 8.9 Hz, each 2H, CHPh), 7.15, 6.85 (d, $^3$J(H—H)=8.8 Hz, each 2H, CHPh), 6.15, 5.60 (m, each 1H, =CH$_2$), 5.53 (m, 1H, CH), 4.29 (m, 4H, CH$_2$O), 1.96 (s, 3H, CH$_3$), 1.66 (s, 3H, CH$_3$), 1.35 (s, 18H, CH$_3$)

$^{13}$C {$^1$H} NMR (125 MHz, CDCl$_3$): δ 166.9 (CO), 156.5, 156.4, 144.0, 143.8 (CPh), 136.1 (C=CH$_2$), 128.0, 126.3, 114.5, 114.2, 114.1 (CHPh), 126.5 (C=CH$_2$), 71.3 (CH), 70.9 (CH$_2$O), 41.8 (C), 34.2 (CBu$^t$), 31.8 (CH$_3$Bu$^t$), 31.5, 18.5 (CH$_3$).

Example 17

D^tBuDMA-CH$_2$

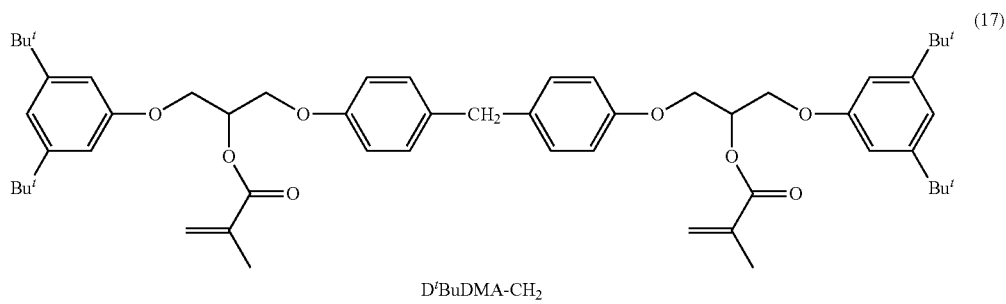

D^tBuDMA-CH$_2$ (17)

IR (KBr, cm$^{-1}$): ν 3103 (=CH$_2$), 3052, 3038 (CH$_{aromatic}$), 2964, 2869 (CH$_{aliphatic}$), 1721 (CO), 1638 (=CH$_2$), 1605, 1592 (C=C$_{aromatic}$)

$^1$H NMR (500 MHz, CDCl$_3$): δ 7.09, 6.88 (m, each 2H, each CHPh), 7.05 (s, 1H, CHPh), 6.79 (s, 2H, CHPh), 6.16, 5.59 (m, each 1H, =CH$_2$), 5.57 (m, 1H, CH), 4.30 (m, 4H, CH$_2$O), 3.89 (Ph-CH$_2$-Ph), 1.96 (s, 3H, CH$_3$), 1.32 (s, 18H, CH$_3$)

$^{13}$C {$^1$H} NMR (125 MHz, CDCl$_3$): δ 166.9 (CO), 158.3, 156.9, 152.5, 134.4 (CPh), 136.1 (C=CH$_2$), 129.9, 115.9, 114.9, 109.3 (CHPh), 126.5 (C=CH$_2$), 71.2 (CH), 66.3 (CH$_2$O), 40.3 (Ph-CH$_2$-Ph), 35.2 (CBu$^t$), 31.6 (CH$_3$Bu$^t$), 18.5 (CH$_3$).

Example 18

BDDMA

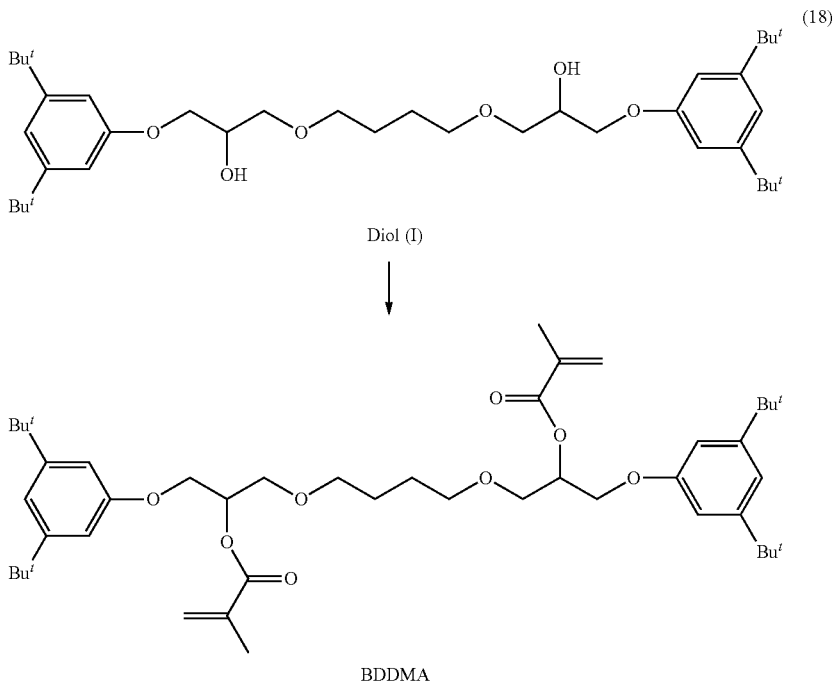

A mixture of 5.08 g (25.1 mmol) of 1,4-butanediol diglycidyl ether, 10.48 g (50.8 mmol) 3,5-di-tert-butyl phenol and 0.023 g triphenylphosphane was stirred at 95° C. for 3 days under nitrogen. The reaction mixture was separated using column chromatography with ethyl acetate/methylene chloride (2:8 by volume) as mobile phase and silica gel as stationary phase. A light yellow product (diol (I)) was obtained after removing the solvent under vacuum. 4.89 g diol (I) (7.95 mmol) was mixed with 1.66 g (16 mmol) triethylamine, 0.23 g 1,5-di-tert-butyl phenol (as inhibitor). 1.72 g (16.5 mmol) methacryloyl chloride dissolved in 30 mL methylene chloride was added to the above mixture dropwise under both ice water bath and nitrogen conditions. After stirring for one day, the mixture was treated with HCl (1M solution) 3*50 mL, saturated $NaHCO_3$ 3*50 mL and then with 2*30 mL distilled water. The organic phase was dried with anhydrous sodium sulfate, filtered and the solvent was removed under vacuum, then separated using column chromatography with ethyl acetate/methylene chloride (2:8 by volume) as mobile phase and silica gel as stationary phase. The final product (BDDMA) was slightly yellow oil.

IR (KBr, $cm^{-1}$): v 3103 (=$CH_2$), 3052 ($CH_{aromatic}$), 2964, 2869 ($CH_{aliphatic}$), 1721 (CO), 1638 (=$CH_2$), 1604, 1592 (C=$C_{aromatic}$)

$^1$H NMR (500 MHz, $CDCl_3$): δ 7.09 (m, 1H, CHPh), 6.83 (s, 2H, CHPh), 6.19, 5.62 (m, each 1H, =$CH_2$), 5.40 (m, 1H, CH), 4.24, 3.79, 3.56 (m, each 2H, $CH_2O$), 2.00 (s, 3H, $CH_3$), 1.49 (s-br, 2H, $CH_2$), 1.36 (s, 18H, $CH_3$)

$^{13}$C {$^1$H} NMR (125 MHz, $CDCl_3$): δ 166.9 (CO), 158.4, 152.4 (CPh), 136.3 (C=$CH_2$), 115.5, 109.4 (CHPh), 126.3 (C=$CH_2$), 77.2 (CH), 72.0, 71.5, 69.2 ($CH_2O$), 35.1 ($CBu^t$), 31.7 ($CH_3Bu^t$), 26.4 ($CH_2$), 18.5 ($CH_3$).

Example 19

Synthesis of Model Monomethacrylate Monomers

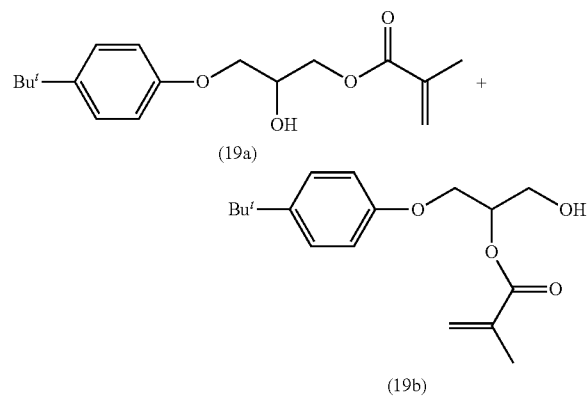

A mixture of 4-tert-butylphenylglycidyl ether 10.3145 g (50 mmol), 4.3045 g (50 mmol) of methacrylic acid, 0.1003 g of triphenylphosphine and 5 mg of 2,6-di-tertbutyl-4-methylphenol was stirred at 85° C. for 18 hours under nitrogen atmosphere. After cooling down the reaction mixture, the brown viscous residue obtained was diluted in $CH_2Cl_2$ and purified by chromatographic on a silica gel column (5×15 cm) with a mixture 80:20/$CH_2Cl_2$:Ethyl acetate. Isomers 19a and 19b were obtained as viscous light yellow oils in a ratio of 86 and 14% respectively determinate by $^1$H NMR.

Data for 19a

IR (KBr, cm$^{-1}$): ν 3447 (OH), 3103 (=CH$_2$), 3036 (CH$_{aromatic}$), 2962-2870 (CH$_{aliphatic}$), 1719 (CO), 1637 (C=C)

$^1$H NMR (500 MHz, CDCl$_3$): δ 7.33, 6.88 (d, $^3$J(H—H)= 8.8 Hz, each 2H, 2 CHPh), 6.18, 5.62 (m, each 1H, =CH$_2$), 4.37-4.06 (m, 5H, CH$_2$O and CHOH), 3.78 (s-br, 1H, OH), 1.98 (s, 3H, CH$_3$), 1.33 (s, 9H, 3 CH$_3$)

$^{13}$C {$^1$H} NMR (125 MHz, CDCl$_3$): δ167.6 (CO), 156.2, 144.2 (CPh), 136.1 (C=CH$_2$), 126.5, 114.2 (CHPh), 126.4 (C=CH$_2$), 68.9, 65.8 (CH$_2$O), 68.7 (CHOH), 34.2 (CBu$^t$), 31.6 (CH$_3$Bu$^t$), 18.4 (CH$_3$)

Data for 19b $^1$H NMR (500 MHz, CDCl$_3$): δ 7.33, 6.88 (dd, $^3$J(H—H)= 4.7, $^5$J(H—H)=2.0 Hz, each 2H, 2 CHPh), 6.13, 5.54 (m, each 1H, =CH$_2$), 5.28 (m, 1H, CHOH), 4.37, 4.00 (m, each 2H, CH$_2$O), 1.97 (s, 3H, CH$_3$), 1.94 (s, 1H, OH), 1.33 (s, 9H, 3 CH$_3$)

$^{13}$C {$^1$H} NMR (125 MHz, CDCl$_3$): δ 167.3 (CO), 156.4, 144.0 (CPh), 136.1 (C=CH$_2$), 126.4, 114.3 (CHPh), 126.5 (C=CH$_2$), 73.5 (CH), 66.6, 62.0 (CH$_2$O), 34.5 (CBu$^t$), 31.9 (CH$_3$Bu$^t$), 18.7 (CH$_3$)

Example 20

Compound 20

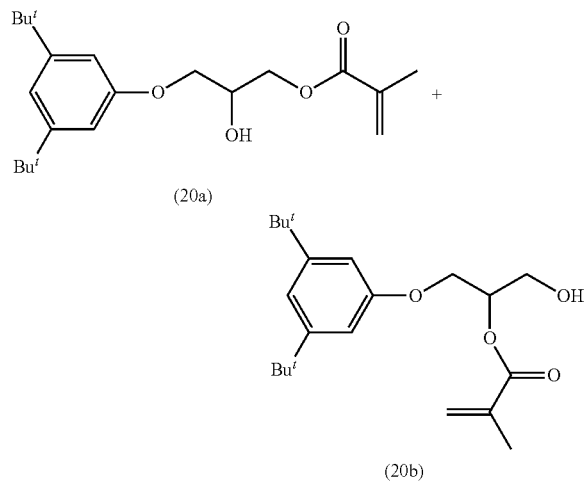

(20a)

(20b)

A mixture of 3,5-di-tert-butylphenol 10.000 g (48.50 mmol), 6.9003 g (48.5 mmol) of glycidyl methacrylate, 0.0510 g of triphenylphosphine and 5 mg of 2,6-di-tertbutyl-4-methylphenol were stirred at 85° C. over night under nitrogen atmosphere. After cooling down the reaction mixture, the brown viscous residue obtained was sublimated to removed the traces of 3,5-di-tert-butylphenol and purified by chromatographic on a silica gel column (5×15 cm) with a mixture 90:10/CH$_2$Cl$_2$:Ethyl acetate. The isomers 20a and 20b were obtained as a mixture; the proportion ratio obtained by $^1$H NMR was 70/30 respectively.

Data for 20a

IR (KBr, cm$^{-1}$): ν 3435 (OH), 3103 (=CH$_2$), 3075 (CH$_{aromatic}$), 2963-2869 (CH$_{aliphatic}$), 1722 (CO), 1638 (C=C)

$^1$H NMR (500 MHz, CDCl$_3$): δ 7.12 (t, $^4$J(H—H)=2.2 Hz, 1H, CHPh), 6.84 (d, $^4$J(H—H)=2.2 Hz, 2H, 2 CHPh), 6.22, 5.65 (m, each 1H, =CH$_2$), 4.48-4.13 (m, 5H, 2 CH$_2$O and C HOH), 3.07 (s-br, 1H, OH), 2.01 (s, 3H, CH$_3$), 1.37 (s, 9H, 3 CH$_3$)

$^{13}$C {$^1$H} NMR (125 MHz, CDCl$_3$): δ167.8 (CO), 158.1, 152.5 (CPh), 136.0 (C=CH$_2$), 126.5 (C=CH$_2$), 115.7, 109.1 (CHPh), 68.9, 65.9 (CH$_2$O), 68.7 (CHOH), 35.1 (CBu$^t$), 31.6 (CH$_3$Bu$^t$), 18.4 (CH$_3$).

Data for 20b $^1$H NMR (500 MHz, CDCl$_3$): δ 7.02 (t, $^4$J(H—H)=2.3 Hz, 1H, CHPh), 6.76 (d, $^4$J(H—H)=2.3 Hz, 2H, 2 CHPh), 6.23, 5.65 (m, each 1H, =CH$_2$), 5.35 (m, 1H, CH), 4.48-4.13 (m, 4H, 2 CH$_2$O), 2.02 (s, 3H, CH$_3$), 2.00 (s, 1H, OH), 1.37 (s, 9H, 3 CH$_3$)

$^{13}$C {$^1$H} NMR (125 MHz, CDCl$_3$): δ167.7 (CO), 158.2, 155.5 (CPh), 136.1 (C=CH$_2$), 126.7 (C=CH$_2$), 115.7, 109.9 (CHPh), 73.7 (CH), 66.5, 62.2 (CH$_2$O), 34.9 (CBu$^t$), 31.6 (CH$_3$Bu$^t$), 18.4 (CH$_3$).

Example 21

Compound 21

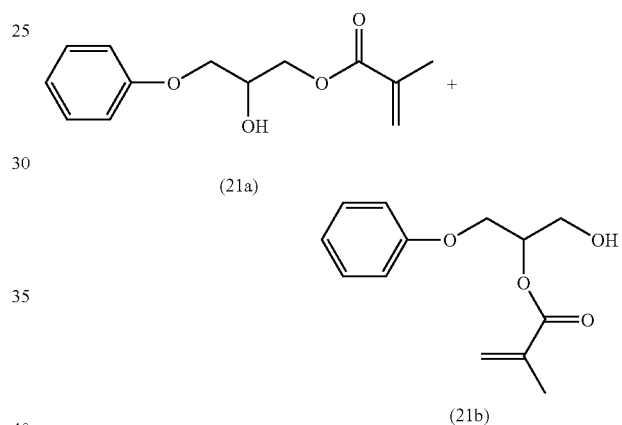

(21a)

(21b)

Route A.

A mixture of glycidyl methacrylate 5.0000 g (35 mmol), 3.6410 g (35.1 mmol) of phenol, 0.0503 g of triphenylphosphine and 5 mg of 2,6-di-tertbutyl-4-methylphenol was stirred at 85° C. for 18 hours under nitrogen atmosphere. After cooling down the reaction mixture, the brown viscous residue obtained was diluted in CH$_2$Cl$_2$ and purified by chromatographic on a silica gel column (5×15 cm) with a mixture 90:10/CH$_2$Cl$_2$:Ethyl acetate. Isomers 21a and 21b were obtained as a mixture; the proportion ratio obtained by $^1$H NMR was 88/12 respectively.

Route B.

A mixture of phenylglycidyl ether 3.0005 g (19.9 mmol), 1.7218 g (20 mmol) of methacrylic acid 0.0103 g of triphenylphosphine and 5 mg of 2,6-di-tertbutyl-4-methylphenol were heated at 85° C. over night. After cooling, the reaction mixture was dissolved in CH$_2$Cl$_2$ and purified by chromatographic column using a mixture 70:30/CH$_2$Cl$_2$: ethyl acetate. Two fractions were collected. The first one was identified by $^1$H NMR as isomer 21a; the second fraction rich in 21b was passed through the column again using a mixture 70:30/ CH$_2$Cl$_2$: ethyl acetate and therefore 21b was obtained pure.

Data for 21a

IR (KBr, cm$^{-1}$): ν 3467 (OH), 3105 (=CH$_2$), 3064-3040 (CH$_{aromatic}$), 2962-2882 (C—H$_{aliphatic}$), 1719 (CO), 1637 (C=C)

¹H NMR (500 MHz, CDCl₃): δ 7.26 (dd, ³J(H—H)=8.8, 7.4 Hz, 2H, CHPh), 7.12 (t, ³J(H—H)=8.7 Hz, 1H, CHPh), 6.89 (d, ³J(H—H)=7.4 Hz, 2H, 2 CHPh), 6.13, 5.56 (m, each 1H, =CH₂), 4.33, 4.01 (m, each 2H, 2 CH₂O), 4.24 (m, 1H, CHOH), 3.17 (s-br, 1H, OH), 1.93 (s, 3H, CH₃)

¹³C {¹H} NMR (125 MHz, CDCl₃): δ 167.5 (CO), 158.4 (CPh), 135.9 (C=CH₂), 129.6, 121.3, 114.6, (CHPh), 126.3 (C=CH₂), 68.8, 65.7 (CH₂O), 68.5 (CHOH), 18.3 (CH₃)

Data for 21b

IR (KBr, cm⁻¹): ν 3446 (OH), 3106 (=CH₂), 3064-3041 (CH$_{aromatic}$), 2960-2882 (C—H$_{aliphatic}$), 1717 (CO), 1636 (C=C)

¹H NMR (500 MHz, CDCl₃): δ 7.30 (dd, ³J(H—H)=8.8, 7.4 Hz, 2H, CHPh), 6.98 (t, ³J(H—H)=8.7 Hz, 1H, CHPh), 6.93 (d, ³J(H—H)=7.4 Hz, 2H, 2 CHPh), 6.17, 5.63 (m, each 1H, =CH₂), 5.28 (m, 1H, CH), 4.22, 3.97 (m, each 2H, 2 CH₂O), 2.07 (s, 1H, OH), 1.97 (s, 3H, CH₃)

¹³C {¹H} NMR (125 MHz, CDCl₃): δ 167.3 (CO), 158.6 (CPh), 136.1 (C=CH₂), 129.8, 121.5, 114.6, (CHPh), 126.7 (C=CH₂), 73.5 (CHOH), 66.5, 62.4 (CH₂O), 18.5 (CH₃)

Example 22

Compound 22

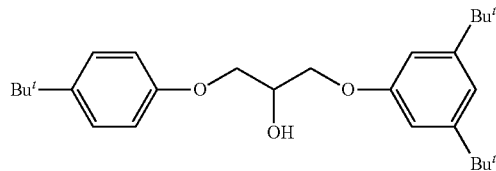

(22)

10.3145 g (49 mmol) of 4-tert-butylphenylglycidyl ether, 11.0394 g (53 mmol) of 3,5-di-tert-butylphenol, 0.1001 g of triphenylphosphine and 5 mg of 2,6-di-tertbutyl-4-methylphenol were heated at 85° C. for 24 hours under nitrogen atmosphere. After cooling down the reaction mixture, the glassy brown residue obtained was heated under vacuum to remove by sublimation the excess of 3,5-di-tert-butylphenol; then dissolved in CH₂Cl₂ and purified by chromatographic on a silica gel column (5×15 cm) with a mixture 80:20/hexane: ethyl acetate.

Data for 22

IR (KBr, cm⁻¹): ν 3421 (OH), 3360, 3041 (CH$_{aromatic}$), 2964, 2904, 2869 (CH$_{aliphatic}$), 1605, 1592 (C=C)

¹H NMR (500 MHz, CDCl₃): δ 7.35, 6.83 (d, ³J(H—H)= 8.9 Hz, each 2H, CHPh), 7.09 (t, ⁴J(H—H)=1.7 Hz, 1H, CHPh), 6.83 (d, ⁴J(H—H)=1.7 Hz, 2H, 2 CHPh), 4.43 (m, 1H, CHOH), 4.20 (m, 4H, 2 CH₂O), 2.88 (s-br, 1H, OH), 1.35 (s, 27H, 9 CH₃)

¹³C {¹H} NMR (125 MHz, CDCl₃): 6158.1, 156.4, 152.5, 144.2 (CPh), 126.5, 115.7, 114.3, 109.2 (CHPh), 69.1 (CHOH), 65.9, 68.8 (CH₂O), 35.2, 34.3 (CBuᵗ), 31.6 (CH₃Buᵗ)

Example 23

Compound 23

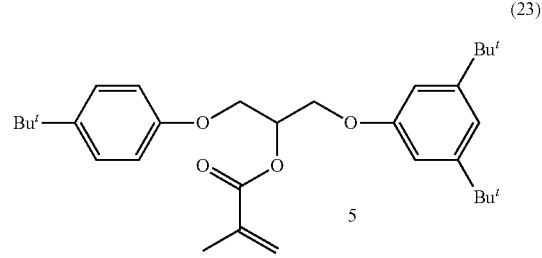

(23)

14.3246 g (35 mmol) of 22 was dissolved in 30 mL of CH₂Cl₂ and 3.512 g (35 mmol) of NEt₃ were added under nitrogen atmosphere. The mixture was cooled at 0° C. and 3.6290 g (37 mmol) dissolved in 20 mL of CH₂CL₂ were added drop wise. Finally, the reaction mixture was stirred at room temperature until next day. The mixture was treated with HCL (1 M solution) 3×10 mL, NaHCO₃ (3×10 mL) and then with distilled water 2×10 mL. The organic layer was dried with NaSO₄, filtered and the solvent was removed under vacuum. The compound was purified by chromatographic column using CH₂Cl₂ as eluent to obtain an oil pale yellow in 91% yield.

Example 24

Properties

Certain embodiments of the present invention were synthesized and evaluated, the results of which are presented in Table 1. The study involved formulation of the dimer acid-based resins including a camphorquinone/amine visible light initiator. Screening studies included monitoring the photopolymerization kinetics by real-time IR. A conventional visible light dental curing unit was used to simulate practical curing conditions. Resins that achieve rapid polymerization and high conversion are desirable. The conversion-dependent onset of phase separation can typically be identified by a baseline shift within the spectral series acquired. The signal transmission before and after polymerization was used as a measure of the degree of transparency/translucency in the polymers. The photopolymerization kinetics and optical properties of the experimental resins are compared in Table 1 with various control resins based on Bis-GMA and TEGDMA. Evaluation of flexural strength, modulus and work of fracture of the polymerized resins and the determination of polymerization shrinkage (again compared against a Bis-GMA/TEGDMA control) was also performed.

The reactants and organic solvents utilized in the synthesis were commercially obtained and used as received with the exception of methylene chloride and ethyl ether which were stirred over calcium hydride and distilled just prior to use. FTIR spectra were acquired on a Nicolet Nexus 670 or in a Perkin Elmer 1420 instruments as a thin film between KBr windows. The ¹H and proton decouple ¹³C NMR spectra were obtained on a Varian Inova 500 MHz or in a JEOL GSX-270 spectrometers using CDCl₃ as the solvent. Camphorquinone (mass fraction 0.2%) and ethyl 4-N,N-dimethylaminobenzeno (mass fraction 0.8%) were added to the monomers and resins to permit photopolymerization with visible light. Stainless steel molds designed to produce bar-shaped specimens (2×2×25 mm) were used for studies. The monomers were clamped in the molds between glass microscope slides and photo-cured for 1 min. each side in a Triad dental light curing (Dentsply) at approximately 65 mW/cm². At the end of the irradiation interval, the intact assembly was aligned in the sample compartment of the FT-IT chamber (Nexus 670, Nocolet). NIR spectra were collected before and within 2 min of the end of each irradiation using 32 coadded scans and 4 wavenumber resolution over the region of 6500 to 4000 cm⁻¹. Conversion values were determined based on the decrease in intensity of the methacrylate C=C stretching mode absorption at 6164 cm⁻¹.

The fully cured polymer specimens (10 to 12 for each monomer or resin) were evaluated in a three-point bending test, which provide flexural strength and modulus characterization. After light polymerization, the specimens were removed from the mold, sanded and stored in distilled water at room temperature for 24 hours before testing. A universal testing machine Model 858 MiniBionix II (MTS System Corp, Eden Praire, Minn.) was used with a 10 mm span and a cross-head speed of 1 mm/min. Samples used for mechanical testing were recovered and utilized to determinate the density of the polymers. The volume of each monomer and polymer was measured by gas pycnometery (Model MVP-60C; Quantachrome Instruments, Boynton Beach, Fla.). The procedure was performed in two stages:

1. Purging to clean up the sample and removing air and moisture from the inside of the chamber is performed by running helium through the chamber at a slow rate for 20 minutes.
2. Measurement of the sample volume by filling the sample cell with helium to the required filling pressure (~17 PSI, Pr). The gas expands in the expansion cell and the final pressure at equilibrium is recorded (Pf).

The volume of the sample is calculated according to the following equation:

$$V\text{sample} = V\text{sample cell} - \{V\text{exp cell}/(Pr/Pf) - 1\}$$

Density was calculated using the weight and the volume obtained for a given sample. Shrinkage measurements were carried out using the ACTA linometer instrument. The monomer samples were placed between a glass slide and an aluminum disk, both coated with a thin layer of grease allowing free radical shrinkage. Axial displacement was measured from the lift of the aluminum disk as recorded by a contact-free transducer system. Water absorption studies were carried out for 2 to 3 specimens of each monomer polymerized between an o-ring mold of 22 mm diameter and 0.5 mm thick. Each homopolymer sample was dried until constant weight in an oven under vacuum at 40° C. and then placed in distilled water until constant weight was attained. Water uptake was calculated from the difference between the final water-equilibrated and the dry sample.

TABLE 1

| SYSTEM (wt ratio) | M.W (g/mol) | Conversion (%) | Shrinkage (%) | Glass transition temp, Tg (° C.) | monomer density (g/cc) | polymer density (g/cc) | Modulus (MPa) |
|---|---|---|---|---|---|---|---|
| 1,6-HDMA | 254 | 76 +/− 2 | 10.70 | | 0.9960 | 1.1150 | |
| BHEDDMA | 789 | 92 +/− 2 | 2.47 +/− 0.13 | −10 | 0.9650 | 0.9690 | 4.16 +/− 0.9 |
| Bis-GMA | 512 | 65 | 4.40 | | 0.1400 | | 3418 +/− 372 |
| BOHDDMA | 849 | 88 +/− 2 | Lin3.3 +/− 0.2 | −17 | 1.0740 | | |
| DAHEMA | 849 | | | | | | |
| DADMA | 673 | 100 +/− 0 | Lin3.4 +/− 0.3 | | 0.9148 | 0.9989 | 25.2 +/− 5.2 |
| DANHDMA | 847 | 96 +/− 2 | | | 0.9910 | 1.0590 | 187 +/− 16 |
| EPBADMA | 554 | 84 +/− 2 | 6.50 | | 1.1080 | | 1906 +/− 245 |
| HEMA/DDI | 847 | 89 | | | | | 79.1 +/− 12.1 |
| mono-BisGMA/DDI | 1059 | 79 | | | | | 67.2 +/− 3.0 |
| OligoBisGMA/DDI | 1100 | | | | | | |
| TEGDMA | 286 | 83 | 13.30 | | 1.0700 | 1.233 | |
| UDMA | 571 | 80 | 5.9 +/− 0.1 | | 1.160 | | 2259 +/− 94 |
| BHEDDM/BDDMA 50:50 | | 84 | 3.8 +/− 0.2 | 44 | | | |
| BHEDDMA/DtBuDMA 25:75 | | 70 | 0.92 +/− 0.38 | | | | |
| BHEDDMA/DtBuDMA 50:50 | | 84 | 2.12 +/− 0.32 | | | | |
| BHEDDMA/MtBuDMA 25:75 | | 70 | 1.77 +/− 0.12 | | | | |
| BHEDDMA/MtBuDMA 50:50 | | 95 | 2.29 +/− 0.10 | | | | |
| BHEDDMA/MtBuDMA 75:25 | | 97 | 2.44 +/− 0.09 | | | | |
| BHEDMA/DtBuDMA 75:25 | | 100 | 2.01 +/− 0.22 | | | | |
| BisGMA/BHEDDMA 39:61 | | 63 | | | | | 181.8 +/− 10.4 |
| BisGMA/BHEDDMA 72:28 | | 59 | | | | | 1612 +/− 218 |
| BisGMA/BOHDDMA 40/60* | | 69 | Lin3.7 +/− 0.1 | 73 | | | |
| BisGMA/BOHDDMA 50:50 | | 65 | Lin3.7 +/− 0.1 | 73 | | | |
| BisGMA/BOHDDMA 60/40* | | 59 | Lin3.0 +/− 0.1 | 68 | | | |
| BisGMA/TEGDMA 50:50 | | 82 +/− 2 | | | | 1.2627 | 2317 |
| BisGMA/TEGDMA 70:30 | | 79 +/− 2 | 5.94 | | | 1.2948 | 2270 |
| BisGMA/TEGDMA 70:30 | | 64.1 +/− 2.8 | 7.26 +/− 0.51 | 89.2 +/− 4.1 | | | 2.3 +/− 0.1 |
| BisGMA/TEGDMA 80:20 | | 73 +/− 3 | | | | | 1319 |
| BOHDDMA/DtBuDMA 40/60 | | 64(1) | 1.8 +/− 0.2 | 46 +/− 1 | | | |
| BOHDDMA/DtBuDMA 50:50 | | 77(4) | 2.7 +/− 0.1 | 53 +/− 1 | | | |
| BOHDDMA/DtBuDMA 60/40 | | 81(1) | 3.1 +/− 0.1 | 58 +/− 1 | | | |
| EBPADMA/BHEDDMA 25/75* | | 87 | Lin4.4 +/− 0.5 | No Peak | | | |
| EBPADMA/BHEDDMA 39:61 | | 86 | | | | | 336.7 +/− 54.9 |
| EBPADMA/BHEDDMA 50/50* | | 84 | Lin4.2 +/− 0.5 | 80 | | | |
| EBPADMA/BHEDDMA 72:28 | | 73 | | | | | 1227 +/− 205 |
| EBPADMA/BHEDDMA 75/25* | | 70 | Lin4.7 +/− 0.6 | | | | |
| EBPADMA/DADMA 50:50* | | 96 +/− 2 | | | | 1.1253 | 579 |
| EBPADMA/DADMA 80:20 | | 87 | | | | 1.1844 | 1319 |

TABLE 1-continued

| | | | | |
|---|---|---|---|---|
| EBPADMA/BOHDDMA 25/75* | 85 | Lin3.6 +/- 0.2 | 85 | |
| EBPADMA/BOHDDMA 50:50* | 76 | Lin3.4 +/- 0.2 | 79 | |
| EBPADMA/BOHDDMA 75/25* | 70 | Lin3.4 +/- 0.2 | 86 | |
| mono-BisGMA-DDI/UDMA | 71 | | | 629.8 +/- 93.4 |
| UDMA/BHEDDMA 37:63 | 90 | | | 135.1 +/- 3.0 |
| UDMA/BHEDDMA 70:30 | 81 | | | 1063 +/- 88 |
| EBPADMA/BOHDDMA/UDMA 65:25:10 | 59.1 +/- 1.1 | | | |
| EBPADMA/BOHDDMA/UDMA 70:17:13 | 77.6 +/- 1.9 | 6.19 +/- 0.17 | 91.8 +/- 8.0 | 1.7 +/- 0.1 |
| EBPADMA/BOHDDMA/UDMA 70:20:10 | 80.1 +/- 1.8 | 6.28 +/- 0.37 | 89.7 +/- 3.5 | 1.6 +/- 0.02 |
| EBPADMA/BOHDDMA/UDMA 75:10:15 | 72.8 +/- 1.1 | | | 1.5 +/- 0.1 |
| UDMA/DADMA/EBPADMA 55:20:25 | 70.1 +/- 1.1 | | | 1.3 +/- 0.1 |
| UDMA/DADMA/EBPADMA 50:20:20 | 75.1 +/- 0.4 | | | 1.4 +/- 0.2 |
| UDMA/DADMA/EBPADMA 65:15:20 | 68.9 +/- 0.8 | | | |

| SYSTEM (wt ratio) | Flex strength (MPa) | Water sorption (wt %) | Water contac angle (deg) | double bond (mol/L) | Phase seperation During Polym'n | stress vs. Bis70/ TEG30 | Shrinkage stress (MPa) |
|---|---|---|---|---|---|---|---|
| 1,6-HDMA | 6.19 +/- 10.0 | 0.58 +/- 0.02 | 65.8 +/- 1.3 | 7.84 | | | |
| BHEDDMA | 8.8 +/- 2.2 | 0.00 | 86.8 +/- 1.4 | 2.43 | | | |
| Bis-GMA | 126 +/- 15 | | 65 | 4.45 | | | |
| BOHDDMA | | | 96 +/- 1 | 2.53 | | | |
| DAHEMA | | | | | | | |
| DADMA | 2.9 +/- 0.2 | 0.05 +/- 0.02 | 86 +/- 3 | 2.72 | | | |
| DANHDMA | 15.0 +/- 0.9 | | 91 | 2.35 | | | |
| EPBADMA | 84.9 +/- 7.3 | 0.70 +/- 0.03 | 76 +/- 1 | 4.00 | | | |
| HEMA/DDI | 19.2 +/- 1.8 | 0.42 +/- 0.03 | 89.5 | | | | |
| mono-BisGMA/DDI | 17.4 +/- 0.9 | 0.21 +/- 0.02 | 79.1 | | | | |
| OligoBisGMA/DDI | | | | | | | |
| TEGDMA | 86 | 5.15 +/- 0.06 | 60.2 +/- 1.1 | | | | |
| UDMA | 126 +/- 8 | 2.87 +/- 0.42 | 55.7 | 3.91 | | | |
| BHEDDM/BDDMA 50:50 | | | | | | | |
| BHEDDMA/DtBuDMA 25/75 | | | | | | | |
| BHEDDMA/DtBuDMA 50:50 | | | | | | | |
| BHEDDMA/MtBuDMA 25:75 | | | | | | | |
| BHEDDMA/MtBuDMA 50:50 | | | | | | | |
| BHEDDMA/MtBuDMA 75:25 | | | | | | | |
| BHEDMA/DtBuDMA 75:25 | | | | | | | |
| BisGMA/BHEDDMA 39:61 | 23.8 +/- 2.4 | 1.17 +/- 0.00 | | | Phase sep b4 cure | | |
| BisGMA/BHEDDMA 72:28 | 83.8 +/- 14.1 | 2.40 +/- 0.00 | | | Phase sep b4 cure | | |
| BisGMA/BOHDDMA 40/60* | | | | | | | |
| BisGMA/BOHDDMA 50:50 | | | | | | | |
| BisGMA/BOHDDMA 60/40* | 35.1 | | | | | | |
| BisGMA/TEGDMA 50:50 | 92 | | | | no | | |
| BisGMA/TEGDMA 70:30 | 82 | 3.00 | | | no | | |
| BisGMA/TEGDMA 70:30 | 92.6 +/- 5.8 | | | | no | 100.0% | 3.43 +/- 0.07 |
| BisGMA/TEGDMA 80:20 | 63 | | | | no | | |
| BOHDDMA/DtBuDMA 40/60 | | | | | | | |
| BOHDDMA/DtBuDMA 50:50 | | | | | | | |
| BOHDDMA/DtBuDMA 60/40 | | | | | | | |
| EBPADMA/BHEDDMA 25/75* | | | | | Yes | | |
| EBPADMA/BHEDDMA 39:61 | 40.6 +/- 3.7 | 0.29 +/- 0.02 | | | | | |
| EBPADMA/BHEDDMA 50/50* | | | | | Yes | | |
| EBPADMA/BHEDDMA 72:28 | 90.7 +/- 4.8 | 0.47 +/- 0.07 | | | Yes | | |
| EBPADMA/BHEDDMA 75/25* | | | | | Yes | | |
| EBPADMA/DADMA 50/50* | 37 | | | | | | |
| EBPADMA/DADMA 80:20 | 63 | | | | | | |
| EBPADMA/BOHDDMA 25/75* | | | | | | | |
| EBPADMA/BOHDDMA 50/50* | | | | | | | |
| EBPADMA/BOHDDMA 75/25* | | | | | | | |
| mono-BisGMA-DDI/UDMA | 58.8 +/- 6.9 | 0.89 +/- 0.05 | 70.9 | | | | |
| UDMA/BHEDDMA 37:63 | 19.5 +/- 3.0 | 1.22* | | | Phase sep b4 cure | | |
| UDMA/BHEDDMA 70:30 | 80.9 +/- 10.9 | 2.39 +/- 0.09 | | | Phase sep b4 cure | | |
| EBPADMA/BOHDDMA/UDMA 65:25:10 | | | | | Phase sep b4 cure | | |
| EBPADMA/BOHDDMA/UDMA 70:17:13 | 74.9 +/- 4.0 | | | | Yes | 76.4% | 2.62 +/- 0.16 |
| EBPADMA/BOHDDMA/UDMA 70:20:10 | 73.7 +/- 0.8 | | | | Yes | 65.3% | 2.24 +/- 0.50 |
| EBPADMA/BOHDDMA/UDMA 75:10:15 | 63.5 +/- 5.2 | | | | Yes | | |
| UDMA/DADMA/EBPADMA 55:20:25 | 62.2 +/- 3.4 | | | | Yes | 88.3% | 3.03 +/- 0.10 |
| UDMA/DADMA/EBPADMA 50:20:20 | 65.5 +/- 7.9 | | | | Yes | 82.5% | 2.83 +/- 0.06 |
| UDMA/DADMA/EBPADMA 65:15:20 | | | | | Yes | | 2.83 +/- 0.06 |

We claim:

1. A ternary polymerizable dental composition comprising
   (a) a dimer acid-derived dimethacrylate monomer;
   (b) a first comonomer that is incapable of acting as a hydrogen-bond donor; and
   (c) a second comonomer that is capable of acting as a hydrogen-bond donor;
   wherein
   the dimer acid-derived dimethacrylate monomer is selected from one of the group consisting of (3-heptyl-4-pentylcyclohexane-1,2-diyl)bis(nonane-9,1-diyl) bis(2-methylacrylate) (DADMA), (((((3-heptyl-4-pentylcyclohexane-1,2-diyl)bis(nonane-9,1-diyl))bis(oxy))bis(carbonyl))bis-(azanediyl))bis(ethane-2,1-diyl)bis(2-methylacrylate) (DANHDMA), (((((3-heptyl-4-pentylcyclohexane-1,2-diyl)bis(nonane-9,1-diyl))bis(oxy))bis(carbonyl))-bis(oxy))bis(ethane-2,1-diyl)bis(2-methylacrylate) (DAHEMA), bis(2-hydroxy-3-(methacryloyloxy)propyl) 9,9'-(3-heptyl-4-pentylcyclohexane-1,2-diyl)dinonanoate (BOHDDMA), (((((3-heptyl-4-pentylcyclohexane-1,2-diyl)bis(nonane-9,1-diyl))bis(azanediyl))bis(carbonyl))bis(oxy))bis(ethane-2,1-diyl)bis(2-methylacrylate) (HEMA/DDI), (((((3-heptyl-4-pentylcyclohexane-1,2-diyl)bis(nonane-9,1-diyl))bis(azanediyl))bis(carbonyl))bis(oxy))bis(3-phenoxypropane-2,1-diyl)bis(2-methylacrylate) (mono-BisGMA/DDI) and oligomeric BisGMA/DDI;
   the first comonomer that is incapable of acting as a hydrogen-bond donor is selected from the group consisting of ethoxylated bisphenol A dimethacrylate (EBPADMA), tetraethylene glycol dimethacrylate, and triethylene glycol dimethacrylate (TEGDMA); and
   the second comonomer that is capable of acting as a hydrogen-bond donor is selected from the group consisting of 2,2-bis[p-(2'-hydroxy-3'-methacryloxypropoxy)phenyl]-propane (BisGMA), urethane dimethacrylate (UDMA), (((((3-heptyl-4-pentylcyclohexane-1,2-diyl)bis(nonane-9,1-diyl))bis(oxy))bis(carbonyl))bis(azanediyl))bis(ethane-2,1-diyl)bis(2-methylacrylate) (DANHDMA), (((((3-heptyl-4-pentylcyclohexane-1,2-diyl)bis(nonane-9,1-diyl))bis(azanediyl))bis(carbonyl))bis(oxy))bis(ethane-2,1-diyl)bis(2-methylacrylate) (HEMA/DDI), (((((3-heptyl-4-pentylcyclohexane-1,2-diyl)bis(nonane-9,1-diyl))bis(azanediyl))bis(carbonyl))bis(oxy))bis(3-phenoxypropane-2,1-diyl)bis(2-methylacrylate) (mono-BisGMA/DDI), and oligomeric BisGMA/DDI; and wherein the dimer acid-derived dimethacrylate monomer is different than the second comonomer.

2. The composition of claim 1 further comprising an initiator.

3. The composition of claim 2 wherein the initiator is in an amount of from about 0.01 to about 5 weight percent based on the total weight of the composition.

4. The composition of claim 2 wherein the initiator is selected from the group consisting of camphorquinone, 2,2-dimethoxy-2-phenylacetone (DMPA) and ethyl 4-N,N-dimethaminobenzoate.

5. The composition of claim 1 wherein the dimer acid-derived dimethacrylate is compatible and capable of hydrogen bonding interactions with either one of the first comonomer or the second comonomer, but incompatible and not capable of hydrogen bonding interaction with the other comonomer.

6. The composition of claim 1 wherein the dimer acid-derived monomer and the comonomers produce microphase-separated, heterogeneous polymeric structures upon polymerization.

7. A photopolymerizable composition comprising:
   (a) a dimer acid-derived dimethacrylate monomer;
   (b) a first comonomer; and
   (c) an initiator; wherein
   the dimer acid-derived dimethacrylate monomer is selected from the group consisting of (3-heptyl-4-pentylcyclohexane-1,2-diyl)bis(nonane-9,1-diyl) bis(2-methylacrylate) (DADMA), (((((3-heptyl-4-pentylcyclohexane-1,2-diyl)bis(nonane-9,1-diyl))bis(oxy))bis(carbonyl))bis(azanediyl))bis(ethane-2,1-diyl)bis(2-methylacrylate) (DANHDMA), (((((3-heptyl-4-pentylcyclohexane-1,2-diyl)bis(nonane-9,1-diyl))bis(oxy))bis(carbonyl))bis(oxy))bis(ethane-2,1-diyl)bis(2-methylacrylate) (DAHEMA), bis(2-hydroxy-3-(methacryloyloxy)propyl) 9,9'-(3-heptyl-4-pentylcyclohexane-1,2-diyl)dinonanoate (BOHDDMA), (((((3-heptyl-4-pentylcyclohexane-1,2-diyl)bis(nonane-9,1-diyl))bis(azanediyl))bis(carbonyl))bis(oxy))bis(ethane-2,1-diyl)bis(2-methylacrylate) (HEMA/DDI), (((((3-heptyl-4-pentylcyclohexane-1,2-diyl)bis(nonane-9,1-diyl))bis(azanediyl))bis(carbonyl))bis(oxy))bis(3-phenoxypropane-2,1-diyl)bis(2-methylacrylate) (mono-BisGMA/DDI) and oligomeric BisGMA/DDI; and
   the first comonomer is selected from the group consisting of 2,2-bis[p-(2'-hydroxy-3'-methacryloxypropoxy)phenyl]-propane (BisGMA), ethoxylated bisphenol A dimethacrylate (EBPADMA), urethane dimethacrylate (UDMA), tetraethyleneglycoldimeth)acrylate, and triethylene glycol dimethacrylate (TEGDMA).

8. The composition of claim 1 wherein the initiator is selected from the group consisting of camphorquinone, 2,2-dimethoxy-2-phenylacetone (DMPA) and ethyl 4-N,N-dimethaminobenzoate.

9. The composition of claim 7 further comprising a second comonomer wherein the dimer acid-derived dimethacrylate is compatible and capable of hydrogen bonding interactions with either one of the first comonomer or the second comonomer, but incompatible and not capable with hydrogen bonding interaction with the other comonomer; wherein the dimer acid-derived dimethacrylate monomer and the comonomers produce a micro-phase separated polymer structure with the optical properties dependent on the phase separated morphology and domain dimensions.

10. The composition of claim 7 wherein the first comonomer and the dimer acid-derived dimethacrylate monomer are selected from the group consisting of:
   2,2-bis[p-(2'-hydroxy-3'-methacryloxypropoxy)phenyl]-propane (BisGMA)/bis(2-hydroxy-3-(methacryloyloxy)propyl) 9,9'-(3-heptyl-4-pentylcyclohexane-1,2-diyl)dinonanoate (BOHDDMA);
   ethoxylated bisphenol A dimethacrylate (EBPADMA)/(3-heptyl-4-pentylcyclohexane-1,2-diyl)bis(nonane-9,1-diyl)bis(2-methylacrylate) (DADMA);
   ethoxylated bisphenol A dimethacrylate (EBPADMA)/bis(2-hydroxy-3-(methacryloyloxy)propyl) 9,9'-(3-heptyl-4-pentylcyclohexane-1,2-diyl)dinonanoate (BOHDDMA); and
   (((((3-heptyl-4-pentylcyclohexane-1,2-diyl)bis(nonane-9,1-diyl))bis(azanediyl))bis(carbonyl))bis(oxy))bis(3- phenoxypropane-2,1-diyl)bis(2-methylacrylate) (mono-BisGMA/DDI)/urethane dimethacrylate (UDMA).

11. The composition of claim 1 wherein the dimer acid-derived dimethacrylate monomer, the first comonomer, and the second comonomer are selected from the group consisting of:
bis(2-hydroxy-3-(methacryloyloxy)propyl)-heptyl-4-pentylcyclohexane-1,2-diyl)dinonanoate (BOHD-DMA)/ethoxylated bisphenol A dimethacrylate (EB-PADMA)/urethane dimethacrylate (UDMA); and
(3-heptyl-4-pentylcyclohexane-1,2-diyl)bis(nonane-9,1-diyl)bis(2-methylacrylate) (DADMA)/ethoxylated bisphenol A dimethacrylate (EBPADMA)/urethane dimethacrylate (UDMA).

12. The composition of claim 1 wherein the weight percent of the dimer acid-derived dimethacrylate monomer in the composition is from 10 wt % to 25 wt % relative to the total combined weight of the dimer acid-derived dimethacrylate monomer, the first comonomer, and the second comonomer in the composition.

13. The composition of claim 1 wherein the weight percent of the first comonomer in the composition is from 20 wt % to 75 wt % relative to the total combined weight of the dimer acid-derived dimethacrylate monomer, the first comonomer, and the second comonomer in the composition.

14. The composition of claim 1 wherein the weight percent of the second comonomer in the composition is from 10 wt % to 65 wt % relative to the total combined weight of the dimer acid-derived dimethacrylate monomer, the first comonomer, and the second comonomer in the composition.

15. The composition of claim 1 wherein the weight percent of the dimer acid-derived dimethacrylate monomer in the composition is from 10 wt % to 25 wt %, the first comonomer in the composition is from 65 wt % to 75 wt %, and the second comonomer in the composition is from 10 wt % to 15 wt % relative to the total combined weight of the dimer acid-derived dimethacrylate monomer, the first comonomer, and the second comonomer in the composition.

16. The composition of claim 15 wherein the dimer acid-derived dimethacrylate monomer is capable of acting as a hydrogen bond donor.

17. The composition of claim 1 wherein the weight percent of the dimer acid-derived dimethacrylate monomer in the composition is from 15 wt % to 20 wt %, the first comonomer in the composition is from 20 wt % to 25 wt %, and the second comonomer in the composition is from 50 wt % to 65 wt % relative to the total combined weight of the dimer acid-derived dimethacrylate monomer, the first comonomer, and the second comonomer in the composition.

18. The composition of claim 17 wherein the dimer acid-derived dimethacrylate monomer is not capable of acting as a hydrogen bond donor.

* * * * *